United States Patent
Møller

(10) Patent No.: US 7,923,031 B2
(45) Date of Patent: Apr. 12, 2011

(54) HAEMOSTATIC SPRAYS AND COMPOSITIONS

(75) Inventor: Lene Møller, Copenhagen (DK)

(73) Assignee: Ferrosan Medical Devices A/S (DK)

( * ) Notice: Subject to any disclaimer, the term of this patent is extended or adjusted under 35 U.S.C. 154(b) by 763 days.

(21) Appl. No.: 10/587,767

(22) PCT Filed: Jan. 28, 2005

(86) PCT No.: PCT/DK2005/000063
§ 371 (c)(1),
(2), (4) Date: Oct. 17, 2006

(87) PCT Pub. No.: WO2005/072700
PCT Pub. Date: Aug. 11, 2005

(65) Prior Publication Data
US 2007/0160543 A1     Jul. 12, 2007

Related U.S. Application Data

(60) Provisional application No. 60/540,005, filed on Jan. 30, 2004, provisional application No. 60/546,972, filed on Feb. 24, 2004.

(51) Int. Cl.
*A61M 35/00* (2006.01)
*A61K 31/728* (2006.01)
*A61K 8/65* (2006.01)
*A61K 9/14* (2006.01)

(52) U.S. Cl. ........ 424/489; 424/499; 530/354; 604/290; 604/67

(58) Field of Classification Search .................. None
See application file for complete search history.

(56) References Cited

U.S. PATENT DOCUMENTS

| | | | |
|---|---|---|---|
| 2,465,357 A | 3/1949 | Correll | |
| 2,465,860 A | 3/1949 | Fleischmann | |
| 2,558,395 A | 6/1951 | Studer | |
| 3,224,434 A | 12/1965 | Molomut et al. | |
| 3,678,933 A | 7/1972 | Moore et al. | |
| 3,815,580 A | 6/1974 | Oster | |
| 3,869,539 A | 3/1975 | Kring et al. | |
| 3,930,052 A | 12/1975 | De brou et al. | |
| 4,098,728 A | 7/1978 | Rosenblatt | |
| 4,265,233 A | 5/1981 | Sugitachi et al. | |
| 4,280,954 A | 7/1981 | Yannas et al. | |
| 4,320,201 A | 3/1982 | Berg et al. | |
| 4,492,305 A | 1/1985 | Avery | |
| 4,515,637 A | 5/1985 | Cioca | |
| 4,522,302 A | 6/1985 | Paikoff | |
| 4,559,304 A | 12/1985 | Kasai et al. | |
| 4,655,211 A | 4/1987 | Sakamoto et al. | |
| 4,696,812 A | 9/1987 | Silbering et al. | |
| 4,735,616 A | 4/1988 | Eibl et al. | |
| 4,749,689 A | 6/1988 | Miyata et al. | |
| 4,851,521 A | 7/1989 | Della valle et al. | |
| 4,861,714 A | 8/1989 | Dean, Jr. et al. | |
| 4,863,856 A | 9/1989 | Dean, Jr. et al. | |
| 4,891,359 A | 1/1990 | Saferstein | |
| 4,982,769 A | 1/1991 | Fournier et al. | |
| 4,997,753 A | 3/1991 | Dean et al. | |
| 5,024,841 A | 6/1991 | Chu et al. | |
| 5,037,740 A | 8/1991 | Tanaka | |
| 5,112,750 A | 5/1992 | Tanaka | |
| 5,149,540 A | 9/1992 | Kunihiro et al. | |
| 5,180,583 A | 1/1993 | Hedner | |
| 5,196,185 A * | 3/1993 | Silver et al. ................... 424/45 |
| 5,356,883 A | 10/1994 | Kuo et al. | |
| 5,387,208 A | 2/1995 | Ashton et al. | |
| 5,394,886 A | 3/1995 | Nabai et al. | |
| 5,399,361 A | 3/1995 | Song et al. | |
| 5,401,511 A | 3/1995 | Margalit | |
| 5,443,481 A | 8/1995 | Lee | |
| 5,456,693 A | 10/1995 | Conston et al. | |
| 5,462,860 A | 10/1995 | Mach | |
| 5,503,848 A | 4/1996 | Perbellini et al. | |
| 5,512,301 A | 4/1996 | Song et al. | |
| 5,595,735 A | 1/1997 | Saferstein et al. | |
| 5,643,596 A | 7/1997 | Pruss et al. | |

(Continued)

FOREIGN PATENT DOCUMENTS
BG        0051589 A1        7/1993

(Continued)

OTHER PUBLICATIONS

Automatic Translation of EP 0737467.
English Derwent abstract of Ranjane reference, Nov. 18, 1997.
Gelfoam RIM product information sheet, Jul. 2007.
Google search result showing disclosure of handled Gelfoam swab in the body of the Kelly publication, accessed online on May 11, 2009.
Kelly M. J. et al., "The value of an operative wound swab sent in transport medium in the prediction of later clinical wound infection: A controlled clinical and bacteriological evaluation", Brit. J. Surgery (1978), 65:2, pp. 81-88.

(Continued)

*Primary Examiner* — Suzanne M Noakes
*Assistant Examiner* — Marsha M Tsay
(74) *Attorney, Agent, or Firm* — Jonathan D. Ball; King & Spalding LLP

(57) ABSTRACT

The present invention is directed to a powder delivery system containing a composition comprising gelatin or collagen powder having a mean particle size of at least 10 μm. The gelatin or collagen powder is typically in dry form, i.e. no liquid components and/or propellants are added to the composition. The present invention is also directed to an improved powder delivery system which contains a protective structure, such as a skirt, located close to the orifice of the delivery system. In a further aspect, the present invention is directed to gelatin- or collagen-based compositions useful in hemostatic applications. In a further aspect of the invention the powder delivery system comprises gelatin or collagen powder in a dry form ready to use. Further the powder delivery system in a dry form might comprise an agent incompatible with moisture and/or water.

25 Claims, 11 Drawing Sheets

U.S. PATENT DOCUMENTS

| | | | |
|---|---|---|---|
| 5,645,849 A | 7/1997 | Pruss et al. |
| 5,660,854 A | 8/1997 | Haynes et al. |
| 5,669,934 A | 9/1997 | Sawyer |
| 5,690,675 A | 11/1997 | Sawyer et al. |
| 5,690,954 A | 11/1997 | Illum |
| 5,700,476 A | 12/1997 | Rosenthal et al. |
| 5,712,161 A | 1/1998 | Koezuka |
| 5,723,308 A | 3/1998 | Mach |
| 5,743,312 A | 4/1998 | Pfeifer |
| 5,749,895 A | 5/1998 | Sawyer et al. |
| 5,791,352 A | 8/1998 | Reich et al. |
| 5,795,330 A | 8/1998 | Tofighi et al. |
| 5,798,091 A | 8/1998 | Klein et al. |
| 5,823,671 A | 10/1998 | Mitchell et al. |
| 5,824,015 A | 10/1998 | Sawyer |
| 5,883,078 A | 3/1999 | Seelich et al. |
| 5,890,610 A | 4/1999 | Jansen et al. |
| 5,895,412 A | 4/1999 | Tucker |
| 5,908,054 A | 6/1999 | Safabash et al. |
| 5,931,165 A | 8/1999 | Reich et al. |
| 5,939,259 A | 8/1999 | Harvey et al. |
| 5,951,531 A | 9/1999 | Ferdman et al. |
| 5,951,583 A | 9/1999 | Jensen et al. |
| 5,957,166 A | 9/1999 | Safabash |
| 5,986,168 A | 11/1999 | Noishiki et al. |
| 6,007,613 A | 12/1999 | Izoret |
| 6,027,741 A | 2/2000 | Cialdi et al. |
| 6,042,262 A | 3/2000 | Hajianpour |
| 6,045,570 A | 4/2000 | Epstein et al. |
| 6,063,061 A | 5/2000 | Wallace et al. |
| 6,066,325 A | 5/2000 | Wallace et al. |
| 6,074,663 A | 6/2000 | Delmotte et al. |
| 6,096,309 A | 8/2000 | Prior et al. |
| 6,099,952 A | 8/2000 | Cercone |
| 6,162,241 A | 12/2000 | Coury |
| 6,168,788 B1 | 1/2001 | Wortham |
| 6,218,176 B1 | 4/2001 | Berthold et al. |
| 6,261,596 B1 | 7/2001 | Li et al. |
| 6,280,727 B1 | 8/2001 | Prior et al. |
| 6,283,933 B1 | 9/2001 | D'Alessio et al. |
| 6,300,128 B1 | 10/2001 | Morota |
| 6,303,323 B1 | 10/2001 | Laskey et al. |
| 6,312,725 B1 | 11/2001 | Wallace et al. |
| 6,334,865 B1 | 1/2002 | Redmond et al. |
| 6,364,519 B1 | 4/2002 | Hughes et al. |
| 6,387,413 B1 | 5/2002 | Miyata et al. |
| 6,454,787 B1 | 9/2002 | Maddalo et al. |
| 6,458,380 B1 | 10/2002 | Leaderman |
| 6,461,325 B1 | 10/2002 | Delmotte et al. |
| 6,495,127 B1 | 12/2002 | Wallace et al. |
| 6,548,081 B2 | 4/2003 | Sadozai et al. |
| 6,620,436 B1 | 9/2003 | Rolf |
| 6,635,272 B2 | 10/2003 | Leaderman |
| 6,638,538 B1 | 10/2003 | Hashimoto et al. |
| 6,649,162 B1 | 11/2003 | Biering et al. |
| 6,706,690 B2 | 3/2004 | Reich et al. |
| 6,716,435 B1 | 4/2004 | Farmer et al. |
| 6,733,774 B2 | 5/2004 | Stimmeder |
| 7,052,713 B2 | 5/2006 | Stimmeder |
| 7,125,860 B1 | 10/2006 | Renier et al. |
| 7,427,607 B2 | 9/2008 | Suzuki |
| 7,435,425 B2 | 10/2008 | Qian et al. |
| 2001/0008636 A1* | 7/2001 | Yamamoto et al. ........... 424/426 |
| 2001/0038848 A1 | 11/2001 | Donda et al. |
| 2001/0041913 A1 | 11/2001 | Cragg et al. |
| 2002/0006429 A1 | 1/2002 | Redmond et al. |
| 2002/0010150 A1 | 1/2002 | Cortese et al. |
| 2002/0010482 A1 | 1/2002 | Watt |
| 2002/0012982 A1 | 1/2002 | Blakesley et al. |
| 2002/0015724 A1 | 2/2002 | Yang et al. |
| 2002/0019062 A1 | 2/2002 | Lea et al. |
| 2002/0025921 A1 | 2/2002 | Petito et al. |
| 2002/0026215 A1 | 2/2002 | Redmond et al. |
| 2002/0039594 A1 | 4/2002 | Unger |
| 2002/0042378 A1 | 4/2002 | Reich et al. |
| 2002/0061842 A1 | 5/2002 | Mansour et al. |
| 2002/0072767 A1 | 6/2002 | Zhu |
| 2002/0111576 A1 | 8/2002 | Greene et al. |
| 2002/0164322 A1 | 11/2002 | Schaufler |
| 2002/0173818 A1 | 11/2002 | Reever |
| 2002/0188196 A1 | 12/2002 | Burbank et al. |
| 2002/0192271 A1 | 12/2002 | Hedner et al. |
| 2002/0193448 A1 | 12/2002 | Wallace et al. |
| 2003/0004449 A1 | 1/2003 | Lafratta et al. |
| 2003/0008831 A1 | 1/2003 | Yang |
| 2003/0009194 A1 | 1/2003 | Saker et al. |
| 2003/0012741 A1 | 1/2003 | Furlan Diego et al. |
| 2003/0028140 A1 | 2/2003 | Greff |
| 2003/0032143 A1 | 2/2003 | Neff et al. |
| 2003/0064109 A1 | 4/2003 | Qian et al. |
| 2003/0095993 A1 | 5/2003 | Bentz et al. |
| 2003/0162708 A1 | 8/2003 | Wolff |
| 2003/0181659 A1 | 9/2003 | Naranda et al. |
| 2003/0232746 A1 | 12/2003 | Lamberti et al. |
| 2004/0076647 A1 | 4/2004 | Beiring |
| 2004/0079763 A1 | 4/2004 | Powell et al. |
| 2004/0101546 A1 | 5/2004 | Gorman et al. |
| 2004/0120993 A1 | 6/2004 | Zhang et al. |
| 2004/0197388 A1 | 10/2004 | Sceusa |
| 2004/0214770 A1 | 10/2004 | Reich et al. |
| 2004/0243043 A1 | 12/2004 | McCarthy et al. |
| 2005/0008632 A1 | 1/2005 | Stimmeder |
| 2005/0031691 A1 | 2/2005 | McGurk et al. |
| 2005/0137512 A1 | 6/2005 | Campbell et al. |
| 2005/0171001 A1 | 8/2005 | Pendharkar et al. |
| 2005/0214277 A1 | 9/2005 | Schaufler |
| 2005/0218541 A1 | 10/2005 | Peng et al. |
| 2005/0245905 A1 | 11/2005 | Schmidt et al. |
| 2006/0002890 A1 | 1/2006 | Hersel et al. |
| 2006/0068013 A1 | 3/2006 | DiTizio et al. |
| 2006/0159733 A1 | 7/2006 | Pendharkar et al. |
| 2006/0189516 A1 | 8/2006 | Yang et al. |
| 2006/0193846 A1 | 8/2006 | Stimmeder |
| 2007/0009578 A1 | 1/2007 | Moller et al. |
| 2007/0025955 A1 | 2/2007 | Lowinger et al. |
| 2007/0264301 A1 | 11/2007 | Cleek et al. |
| 2007/0264302 A1 | 11/2007 | Cleek et al. |
| 2008/0095830 A1 | 4/2008 | Van Holten |
| 2008/0311172 A1 | 12/2008 | Schapira et al. |
| 2009/0087569 A1 | 4/2009 | Fan et al. |

FOREIGN PATENT DOCUMENTS

| | | | |
|---|---|---|---|
| BG | 0099900 A | 3/1997 |
| DE | 3146841 | 6/1983 |
| DE | 4119140 | 12/1992 |
| DE | 4407875 | 9/1995 |
| EP | 0156649 | 10/1985 |
| EP | 0341745 B | 11/1989 |
| EP | 0365705 | 5/1990 |
| EP | 0372966 | 11/1990 |
| EP | 0395758 | 11/1990 |
| EP | 0478827 | 4/1992 |
| EP | 0702081 | 3/1996 |
| EP | 0737467 | 10/1996 |
| EP | 0773740 | 11/1999 |
| EP | 1005874 B | 6/2000 |
| EP | 1022031 | 7/2000 |
| EP | 1044693 | 10/2000 |
| EP | 1053758 | 11/2000 |
| EP | 1140235 | 10/2001 |
| EP | 1174463 A | 1/2002 |
| EP | 1258256 | 11/2002 |
| EP | 0790823 | 7/2003 |
| EP | 0891193 | 8/2003 |
| EP | 1095064 | 6/2005 |
| EP | 1095064 B | 6/2005 |
| EP | 1059957 | 8/2007 |
| FR | 2679772 | 5/1993 |
| FR | 2759980 | 8/1998 |
| GB | 697603 | 9/1949 |
| GB | 648619 | 1/1951 |
| GB | 1584080 | 2/1981 |
| GB | 2266239 | 10/1993 |
| GB | 2393120 A | 3/2004 |
| GB | 2414021 | 11/2005 |
| JP | 60214728 | 10/1985 |
| JP | 62070318 | 3/1987 |

| | | |
|---|---|---|
| JP | 62 221357 | 9/1987 |
| JP | 01 130519 | 5/1989 |
| JP | 06254148 | 9/1994 |
| JP | 10-507666 | 7/1998 |
| JP | 2002-513308 | 5/2002 |
| JP | 2004-002271 | 1/2004 |
| WO | WO 89/02730 | 4/1989 |
| WO | WO 9013320 | 11/1990 |
| WO | WO 9306802 | 4/1993 |
| WO | WO 9306855 | 4/1993 |
| WO | WO 9310768 | 6/1993 |
| WO | WO 9321908 | 11/1993 |
| WO | WO-9408552 | 4/1994 |
| WO | WO 9417840 | 8/1994 |
| WO | WO 9512371 | 5/1995 |
| WO | WO 9525748 | 9/1995 |
| WO | WO 9531955 | 11/1995 |
| WO | WO 9607472 | 3/1996 |
| WO | WO 9616643 | 6/1996 |
| WO | WO 9640033 | 12/1996 |
| WO | WO 9717023 | 5/1997 |
| WO | WO 9717024 | 5/1997 |
| WO | WO 9717025 | 5/1997 |
| WO | WO 9729792 | 8/1997 |
| WO | WO 9737694 | 10/1997 |
| WO | WO 9831403 | 7/1998 |
| WO | WO 9836784 | 8/1998 |
| WO | WO 9843092 | 10/1998 |
| WO | WO 9844963 | 10/1998 |
| WO | WO 9851282 | 11/1998 |
| WO | WO 9904828 | 2/1999 |
| WO | WO 9912032 | 3/1999 |
| WO | WO 9944901 | 9/1999 |
| WO | WO 9945938 | 9/1999 |
| WO | WO 0009018 | 2/2000 |
| WO | WO 0018301 | 4/2000 |
| WO | WO 0027327 | 5/2000 |
| WO | WO 0061201 | 10/2000 |
| WO | WO 0074742 | 12/2000 |
| WO | WO 0076533 | 12/2000 |
| WO | WO 0113956 | 3/2001 |
| WO | WO 0128603 | 4/2001 |
| WO | WO 0134206 | 5/2001 |
| WO | WO 0154735 | 8/2001 |
| WO | WO 0166161 A | 9/2001 |
| WO | WO 0197826 | 12/2001 |
| WO | WO 0218450 | 3/2002 |
| WO | WO 0222059 | 3/2002 |
| WO | WO 0240068 | 5/2002 |
| WO | WO 02058749 | 8/2002 |
| WO | WO 03/007845 | 1/2003 |
| WO | WO 03007845 | 1/2003 |
| WO | WO 03055531 | 7/2003 |
| WO | WO 03/070110 | 8/2003 |
| WO | WO 03094983 | 11/2003 |
| WO | WO 2004028404 | 4/2004 |
| WO | WO 2004028423 | 4/2004 |
| WO | WO 2004028583 | 4/2004 |
| WO | WO 2004029095 | 4/2004 |
| WO | WO 2004030711 | 4/2004 |
| WO | WO 2004035629 | 4/2004 |
| WO | WO2004053051 | 6/2004 |
| WO | WO 2004108035 | 12/2004 |
| WO | WO 2005000265 | 1/2005 |
| WO | WO 2005009225 | 2/2005 |
| WO | WO 2005041811 | 5/2005 |
| WO | WO 2005044285 | 5/2005 |
| WO | WO 2005062889 | 7/2005 |
| WO | WO 2006034568 | 4/2006 |
| WO | WO 2006063758 | 6/2006 |
| WO | WO 2007133699 | 11/2007 |
| WO | WO 2008051758 | 5/2008 |
| WO | WO 2008090555 | 7/2008 |
| WO | WO 2009109963 | 9/2009 |

OTHER PUBLICATIONS

Stuart Transport medium information sheet, accessed online on May 27, 2009.
Y.S. Choi et al., "Studies on gelatin-sponges, Part III: A Comparative Study of Cross-Linked Gelating/Alginate, Gelatin/Hyaluronate and Chitosan/Hyaluronate Sponges and Their Application as a Wound Dressing in Full-Thickness Skin Defect of Rat," J. of Materials Sci.: Mat. In Med., vol. 12, 2001, pp. 67-73.
Soules et al, Am. J. Obstet. Gynecl., vol. 143, p. 829-834, 1982, "The prevention of postoperative pelvic adhesions: An animal study comparing barrier methods with Dextran 70".
Maxson et al, Gynecol. Obestet. Invest., vol. 26, p. 160-165, 1988, "Efficacy of a modified oxidized cellulose fabric in the prevention of adhesion formation".
Ouintavalla et al., Biomaterials Jan. 2002;23(1):109-119. Fluorescently labeled mesenchymal stem cells (MSC)maintain multilineage potential and can be detected following articular cartilage defects.
Ellegala et al, Neurosurgery, Aug. 2002, vol. 51, p. 513-516, "Use of FloSeal Hemostatic Sealant In Transsphenoidal Pituitary surgery: technical note".
Choi YS et al, J Biomed Mater Res 1999; 48 (5), p. 631-639, "Studies on gelatin-containing artificial skin: II. Preparation and characterization of cross-linked gelatin-hyaluronate sponge".
Laurent et al, Am. J. Otolaryngol, vol. 7, p. 181-186, 1986, "Hyaluronic acid reduces connective tissue formation in middle ears filled with absorbable gelatin sponge: an experimental study".
Kocak, et al., Fertility and Sterility, vol. 72, No. 5, p. 873-878, Nov. 1999, "Reduction of adhesion formation with cross-linked hyaluronic acid after peritoneal surgery in rats".
Hill-West, et al., Fertility and Sterility, vol. 62, No. 3, p. 630-634, "Efficacy of a resorbable hydrogel barrier, oxidized regenerated cellulose and hyaluronic acid in the prevention of ovarian adhesions in a rabbit model", 1994.
Changez et al, Biomaterials, 2005, vol. 26, No. 14, p. 2095-2104, "Efficacy of antibiotics-loaded interpenetrating network (IPNs) hydrogel eased on poly (acrylic acid) and gelatin for treatment of experimental osteomyelitis: in vivo study".
Raftery, Br. J. Surg., vol. 67, p. 57-58, 1980, "Absorbable Haemostatic materials and intraperitoneal adhesion formation".
Shushan, et al., Journal of Reproductive Medicine, vol. 39, p. 398-402, 1994, "Hyaluronic acid for preventing experimental postoperative intraperitoneal adhesions".
Larsson, et al., Acta Chir. Scand., vol. 26, p. 375-378, 1978, "Surgicel- An absorbable hemostatic material- In prevention of peritoneal adhesions in rats".
Dembo, M. A et al, Lech. Prep. Krovi. Tkanei, p. 139-40, 1974, "Antiseptic hemostatic preparations, their properties and study".
Van Der Salm T.J. et al, J. of Thoracic and Cardiovascular Surgery, 1989, vol. 98, No. 4, p. 618-622, "Reduction of sternal infection by application of topical vancomycin".
Reijnen, et al., Arch Surg., vol. 134, pp. 997-1001, Sep. 1999, "Prevention of Intra-Abdominal Abscesses and adhesions using a hyaluronic acid solution in a rat peritonitis model".
Wachol-Drewek et al, Blomaterials 17, p. 1733-1738, 1996, "Comparative Investigation of drug delivery of collagen implants saturated in antibiotic solutions and a sponge containing gentamicin".
"FloSeal Matrix Hemosealant. Instructions for use". Accessed online Aug. 17, 2005 at http://www.ctsnet.org/file/vendors/931/pdf/140.pdf.
Drognitz et al, Indection Germany (Munich), 2006, 34 (1), p. 29-34, "Release of vancomycin and teicoplanin from a plasticized and resorbable gelatin sponge: in vitro investigation of a new antibiotic delivery system with glycopeptides".
De Iaco, et al., Surgery, vol. 130, p. 60-64, 2001, "Efficacy of a Hyaluronan Derivative gel in postsurgical adhesion prevention in the presence of inadequate hemostasis".
Sakurabayashi etal., Gastroenterological Endoscopy 30(10) Oct. 1988. Clinical evaluation of new hemostatic agent for hemostasis from biopsy wounds in the liver.
Luengo, et al., , Fertility and Sterility, vol. 29, No. 4, Apr. 1978, "Prevention of peritoneal adhesions by the combined use of Spongostan and 32% Dextran 70: an experimental study in pigs".
Spence et al.. Cancer Feb. 1975;35(2).326-341. Cerebellar capillary hemangioblastoma: its histogenesis studied by organ culture and electron microscopy.

Hong et al, Biomaterials, 2001, 22 (20), p. 2777-2783, "Study on gelatin-containing artificial skin IV: a comparative study on the effect of antibiotic and EGF on cell proliferation during epidermal healing".

Oz et al, Ann Thorac Surg 2000, vol. 69, p. 1376-1382, 2000, "Controlled clinical trial of a novel hemostatic agent in cardiac surgery".

West, et al., The Journal of reproductive medicine, vol. 41, p. 149-154, 1996, "Efficacy of adhesion barriers, resorbable hydrogel, oxidized regenerated cellulose and hyaluronic acid".

Sanfilippo et al, Fertility and sterility, vol. 33, No. 3, p. 311-316, Mar. 1980, "Comparison of avitene, topical thrombin and Gelfoam, as sole hemostatic agent in tuboplasties".

Wiesenthal et al, The Journal of Otolaryngology, 1999, vol. 28, No. 5, p. 260-265, "New method for packing the external auditory canal, middle ear space, and mastoid cavities after otologic surgery".

Hae-Won et al, J. of Biomedical Materials Research, 2005, 74B (2), p. 686-698, "Porous scaffolds of gelatin-hydroxyapatite nanocomposites obtained by biometic approach: Characterization and antibiotic drug release".

Li, et al., Arch Otolaryngol Head Neck Surg., vol. 127, p. 534-539, May 2001, "Evaluation of Esterified Hyaluronic Acid as middle ear-packing material".

Yuesong et al, Intern. des Services de San. des Forces Armees, Sep. 1999, vol. 72, No. 7-9, p. 194-196, "Design and experimental study of a slow-release antibiotic membrane implant in surgery wound".

Hill et al, J. Thorac Cardiovasc Surg 1994, vol. 108, p. 1151-1152, "Use of microfibrillar collagen hemostat (Avitenet) and thrombin to achieve hemostats after median sternotomy".

Derwent Abstract Accession No. 1998-046967, English abstract of JP 09296004, published Nov. 18, 1997.

Gelfoam® product information sheet, Pfizer, Jul. 2007.

Google Search, "handled gelfoam swab," downloaded from <<http://www.google.com>>, accessed online on May 11, 2009.

"Stuart Transport Medium," Catalog Item 1518, p. 215, downloaded from <<http://www.condalab.com>>, accessed online on May 27, 2009.

Min et al. "Molecular Weight Changes of Sodium Hyaluronate Powder and Solution by Heat treatment," Matrix Biology Institute, Proceedings of Hyaluronan, Oct. 11-16, 2003.

M.G. Cascone et al.; "Collagen and hyaluronic acid based polymeric blends as drug delivery systems for the release of physiological concentrations of growth hormone." Journal of Materials science: Materials in Medicine; No. 5, 1994; pp. 770-774.

Oz et al.; "Controlled clinical trial of a novel hemostatic agent in cardiac surgery."; Ann Thorac Surg. 2000; vol. 69; 2000; pp. 1376-1382.

Branski et al.; "Mucosal Wound Healing in a Rabbit Model of Subglottic Stenosis"; Arch Otolaryngol Head Neck Surg, vol. 131, Feb. 2005, p. 153-157.

Purdy et al.; "Microfibrillar collagen model of canine cerebral infarction"; Stroks, vol. 20 No. 10, Oct. 1989, p. 1361-1367.

Santomaso et al.; "Powder flowability and density ratios: the impact of granules packing". Chemical Engineering Science 58 (2003) 2857-2874.

Swann; "Studies on hyaluronic acid—I. The preparation and properties of rooster comb hyaluronic acid". Biochemica et biophysica acta, 156 (1968) p. 17-30.

* cited by examiner

HAEMOSTATIC SPRAYS AND COMPOSITIONS

CROSS REFERENCE TO RELATED APPLICATIONS

This application is a United States national phase filing under 35 U.S.C. §371 of International Application No. PCT/DK2005/000063, filed Jan. 28, 2005, which claims priority to United States Provisional Patent Application No. 60/540,005, filed Jan. 30, 2004, and to United States Provisional Patent Application No. 60/546,972, filed Feb. 24, 2004.

FIELD OF THE INVENTION

The present invention is directed to a powder delivery system containing a composition comprising gelatine or collagen powder having a mean particle size of at least 10 µm. The gelatine or collagen powder is typically in dry form, i.e. no liquid components and/or propellants are added to the composition. The present invention is also directed to an improved powder delivery system which contains a protective structure, such as a skirt, located close to the orifice of the delivery system. In a further aspect, the present invention is directed to gelatine- or collagen-based compositions useful in haemostatic applications.

BACKGROUND OF THE INVENTION

WO 01/28603 relates to an injectable formulation for delivery of a composition comprising an osteogenic protein and a haemostatic gelatine foam paste as well as to a method of making a haemostatic gelatine foam paste suitable for injecting osteogenic protein, the method comprising hydration of Gelfoam® powder with glutamic acid buffer.

U.S. Pat. No. 5,394,886 relates to a skin biopsy plug wherein the plug is a porous sponge made from gelatine material, which is implanted into a wound, swells, absorbs blood, and is completely absorbed in the patient. It relates to a combination of the punch (the blade for excising skin) and the plug. The plug used is the commercially available Gelfoam®.

GelFoam® is a commercially available product providing powdered gelatine for application to bleeding surfaces as a haemostatic agent. The powdered gelatine is provided in a full glass jar with a metal lid or in a sachet, each of which are to be opened and the contents of which, i.e. the gelatine, are to be poured into a sterile beaker or bowl.

U.S. Pat. No. 5,645,849 claims a haemostatic patch comprising a biodegradable gelatine matrix, a haemostatic-promoting amount of thrombin and epsilon aminocaproic acid.

JP 62221357 discloses a skin ointment for promoting a haemostatic effect comprising thermoplastic resin or rubber dissolved in solvent and contains dispersed gelatine powder. The product is an ointment comprising thermoplastic resin or rubber and a fine powder of collagen, gelatine or chitosan.

FR 2679772 relates to particulate material to create an embolism comprising a polymer coated with a haemostatic or thrombonic agent. The haemostatic agent may be a finely divided gelatine powder.

U.S. Pat. No. 6,096,309 relates to a haemostatic composition comprising thrombin and a mixture of non-microfibrillar collagen and microfibrillar collagen in an aqueous medium wherein the microfibrillar collagen has an average fibril diameter of about 3-30 nm.

U.S. Pat. No. 4,515,637 relates to both a method of forming a collagen-thrombin haemostatic composition and to a lyophilised collagen product, comprising collagen and thrombin.

U.S. Pat. No. 6,045,570 relates to a gelatine powder for use as a haemostatic agent and to a biological sealant comprising a gelatine slurry which includes milled gelatin powder. The slurry preferably comprises Gelfoam® powder mixed with a diluent selected from saline and water. The slurry demonstrates superior flow characteristics in that it exhibits minimal dilatency and can be easily injected or introduced through catheter lumens, especially small lumens. The product therefore has very fluid characteristics.

U.S. Pat. No. 6,060,461 relates to particles, in particular dextran particles, having a particle size from 0.5-1000 µm and an average pore diameter from 0.5-1000 nm. It is disclosed that such particles may be used for enhancing clot formation on a wound by administering the particles in the form of a dry powder.

U.S. Pat. No. 3,930,052 relates to cold-water-soluble gelatine compositions of different particle size.

U.S. Pat. No. 5,225,536 is directed to particles of gelatine and amino acids. It is stated that such particles are suitable for being blended with various resins. The particle size distribution is so that most particles have a particle size of from 1.5 to 9.0 µm.

US 2003/0012741 relates to a process for preparing micronised collagen. It is stated that the particle size should not exceed 20 µm in order to optimise adhesion to the wound surface.

Various haemostatic sprays are commercially available:

Traumacel S® is a haemostatic dusting powder in a pressurised spray, the active component being a hydrogen calcium salt of oxidised cellulose.

Traumacel P® is a is a powdered haemostatic agent comprising a calcium salt of oxidised cellulose (carboxymethylcellulose calcium) which is applied as dry powder onto a bleeding area.

Avitene® is a microfibullar collagen haemostat "flour" typically applied dry.

Arista® is a haemostatic spray based on microporous polysaccharide hemospheres as described in U.S. Pat. No. 6,060,461 (see above).

SUMMARY OF THE INVENTION

In a first aspect, the present invention relates to a powder delivery system containing a chamber storing a composition comprising gelatine or collagen powder having a mean particle size of at least 10 µm, said chamber having at least one discharge opening sized for distributing said composition.

In another aspect, the present invention relates to a powder delivery system containing a chamber storing a composition consisting of gelatine or collagen powder having a mean particle size of at least 10 µm, said chamber having at least one discharge opening sized for distributing said composition.

In a further aspect, the present invention relates to a composition as defined herein, as well as to a composition as defined herein for use as a medicament. In an interesting embodiment of the invention the composition is in the form of a gel.

In an even further aspect, the present invention relates to a method of promoting haemostasis in a patient in need thereof, said method comprising spraying a composition as defined herein onto at least a portion of the area where bleeding occurs.

In a still further aspect, the present invention relates to the use of gelatine or collagen powder having a mean particle size of at least 10 μm for the manufacture of a composition as defined herein for promoting haemostasis, wherein said composition is sprayed onto at least a portion of the area where bleeding occurs.

Moreover, the present invention also relates to gelatine or collagen powder compositions obtainable by or obtained by the method of the invention.

The present invention also relates to a powder delivery system containing a chamber for storing a powder composition, said chamber comprising at least one discharge opening sized for distributing said composition and a protective structure arranged at the discharge opening.

DETAILED DESCRIPTION OF THE INVENTION

The present invention concerns a "ready-to-use" haemostatic spray which may be used acute as well as prophylactic. One advantage of using a haemostatic spray as compared to the more traditionally used sponges is that the haemostatic agent (in this case gelatine or collagen) can be applied in a thin layer over a relatively large area and that it may be applied to areas of the body that can be hard to reach with traditional sponges.

Although haemostatic sprays based on oxidised cellulose do exist there is a need for haemostatic sprays which contain a material suitable for effecting haemostasis and, at the same time, is more biocompatible than is oxidised cellulose. The present inventor provides a haemostatic spray based on micronised and/or finely pulverised particles of gelatine or collagen. Evidently, gelatine and collagen resembles the skin components to a much higher degree than do oxidised cellulose. Consequently, the haemostatic spray disclosed herein is considered safer and may provide fewer side effects, such as inflammation caused by a response from the immune system, than will haemostatic sprays based on oxidised cellulose.

In addition, the micronised and/or finely pulverised particles disclosed herein have a significantly higher wetability as compared to the conventionally used particles. As wetability is closely related to the capability of absorbing liquids, such as blood, the powder is providing for an improved haemostatic effect compared to conventionally used powder, such as gelatine powder.

In the present context, the term "micronised and/or finely pulverised" is intended to mean particles reduced in size to a mean particle size of less than about 250 μm.

As the price of gelatine is approximately one-third of the price of collagen, gelatine is preferred over collagen for economical reasons.

Gelatine or Collagen Powder

The present inventor has found that the micronised and/or finely pulverised particles of gelatine or collagen powder produced by the method disclosed herein have a small mean particle size. Thus, compared to traditional sponges or powders, a lower amount of gelatine or collagen may be needed to obtain haemostasis when administered in the form of a spray, due to a faster and more efficient haemostasis. Surprisingly, a dramatic improvement of the wetability of the powder was found when testing the powder by the in vitro wetability method described in the experimental section, i.e. the powder disclosed herein was found to absorb the applied liquid instantly. The improvement of wetability is likely to have a similar effect on the absorption capacity of the powder and consequently on the haemostatic effect. The mechanism of the improved effect is not fully understood, though the effect may result from the small particle size which facilitates the access of the blood to the particles. Furthermore, the improved effect might be caused by a high surface area.

From the results obtained by the wetability test as illustrated in FIGS. 9 and 10, it is evident that the wetability is remarkably improved in the powder according to the invention. The skilled person will understand that the wetability of the powder relates to the absorption of a liquid, such as blood. Further it will be understood that a powder with an improved wetability provides for a more efficient haemostatic effect. As the improved powder has a higher wetability the amount of liquid, such as blood, absorbable will be higher providing for an efficient haemostatic effect. The skilled person will understand that there is a correlation between a powder capable of absorbing relative large amounts of liquids and a high wetability.

Figure 1A:
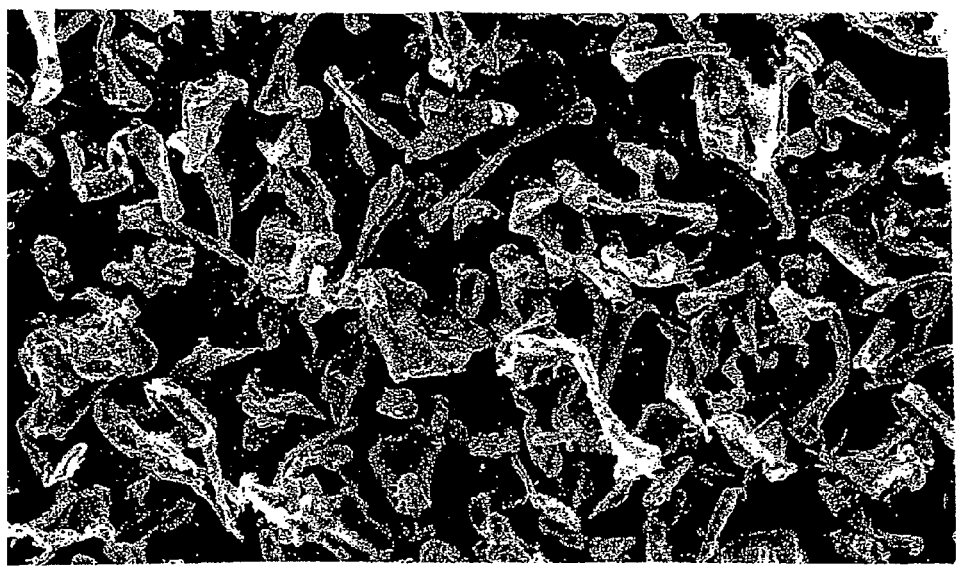

Although gelatine or collagen are currently the preferred materials, it will be understood by the skilled person that in principle any biologically absorbable material may be used for the purposes described herein. Thus, materials other than gelatine or gelatine may be any material, which is known to be suitable for preparation of sponges and powder and, at the same time, being biologically absorbable. Examples of suitable biologically absorbable materials include (in addition to gelatine and collagen) chitin, chitosan, alginate, cellulose, polyglycolic acid, polyacetic acid and mixtures thereof. It will be understood that various forms thereof, such as linear or cross-linked forms, salts, esters and the like may also be used as the biologically absorbable material to be included in the haemostatic powder of the invention.

"Biologically absorbable" is a term which in the present context is used to describe that the materials of which the said powder are made can be degraded in the body to smaller molecules having a size which allows them to be transported into the blood stream. By said degradation and absorption the said powder materials will gradually be removed from the site of application. For example, denatured gelatine can be degraded by proteolytic tissue enzymes to absorbable smaller molecules, whereby the denatured gelatine powder when applied in tissues typically is absorbed within about 3-6 weeks and when applied on bleeding surfaces and mucous membranes typically within 3-5 days.

In a preferred embodiment of the invention, the biologically absorbable material is gelatine. Gelatine is preferred since gelatine is highly biologically absorbable. Furthermore, gelatine is highly biocompatible, meaning that it is non-toxic to an animal, such as a human being, when/if entering the blood stream or being in long-term contact with human tissues.

The gelatine typically originates from a porcine source, but may originate from other animal sources, such as from bovine or fish sources. The gelatine may also be synthetically made, i.e. made by recombinant means.

The collagen typically originates from a bovine source, but may originate from other animal sources. The collagen may also be synthetically made, i.e. made by recombinant means.

As mentioned above, the surface area is an important parameter of the gelatine or collagen powder/particles and, generally, the specific surface area is preferably at least 0.25 m²/g (e.g. 0.25-3.00 m²/g or 0.25-2.00 m²/g) such as at least 0.50 m²/g (e.g. 0.50-3.00 m²/g or 0.50-2.00 m²/g), more preferably at least 0.75 m²/g (e.g. 0.75-3.00 m²/g or 0.75-2.00 m²/g), such as at least 0.80 m²/g (e.g. 0.80-3.00 m²/g or 0.80-2.00 m²/g). In some particular interesting embodiments, the specific surface area is at least 0.90 m²/g (e.g. 0.90-3.00 m²/g or 0.90-2.00 m²/g), such as at least 1.00 m²/g (e.g. 1.00-3.00 m²/g or 1.00 to 2.00 m²/g). In even further embodiments of the invention, the specific surface area may be at least 1.25 m²/g (e.g. 1.25-3.00 m²/g or 1.25-2.00 m²/g), such as at least 1.50 m²/g (e.g. 1.50-3 m²/g or 1.50-2.00 m²/g). The specific surface is conveniently determined by gas adsorption (BET)

As will be acknowledged by the skilled person, a powder with a very small particle size, such as a mean particle size of less than about 10 μm, will give cause technical problems due to poor flowability. Further will a very small particle size give problems with dust while applying the powder. Therefore, the mean particle size of the powder must therefore be a compromise between particles of a mean particle size of at least 10 μm. On the other hand, the particles should not be too large, i.e. the particles should have a mean particle size of less than 250 μm. Thus, in a preferred embodiment of the invention, the mean particle size of the powder is at least 20 μm, such as at least 30 μm, e.g. at least 40 μm, more preferably at least 50 μm, such as at least 60 μm, e.g. at least 70 μm. Analogously, the mean particle size of the powder is preferably less than 200 μm, such as less than 175 μm, e.g. less than 150 μm, more preferably less than 125 μm, such as less than 100 μm, e.g. less than 90 μm.

Stated differently, the mean particle size is in the range of 10-250 μm, such as in the range of 20-250 μm, e.g. in the range of 30-250 μm. In a preferred embodiment of the invention, the mean particles size is in the range of 20-200 μm, such as in the range of 30-175 μm, e.g. in the range of 40-175 μm, more preferably in the range of 50-150 μm, such as in the range of 55-125 μm, e.g. in the range of 60-100 μm. Most preferably, the mean particle size is in the range of 70-90 μm.

When used herein, the term "mean particle size" is defined with reference to the examples provided herein, i.e. the mean particle size is based on laser diffraction measurements.

Conventionally used gelatine powder, such as Surgifoam® Powder, has a particle size distribution where:
10% by volume is less than approximately 90 μm,
50% by volume is less than approximately 350 μm, and
90% by volume is less than approximately 700 μm.

The particles described herein preferably have a particle size distribution so that at least 90% by volume of the particles have a particle size below 250 μm, such as below 200 μm, e.g. below 190 μm, more preferably below 180 μm, such as below 170 μm. In addition, the particle size distribution is preferably so that at least 90% by volume of the particles have a particle size above 5 μm, such as above 10 μm, e.g. above 12 μm, in particular above 15 μm. In other words, the particle size distribution is preferably so that at least 80% by volume of the particles have a particle size of 5-250 μm, preferably of 5-200 μm, such as of 10-190 μm, e.g. of 12-180 μm, in particular of 15-170 μm.

Figure 1B:
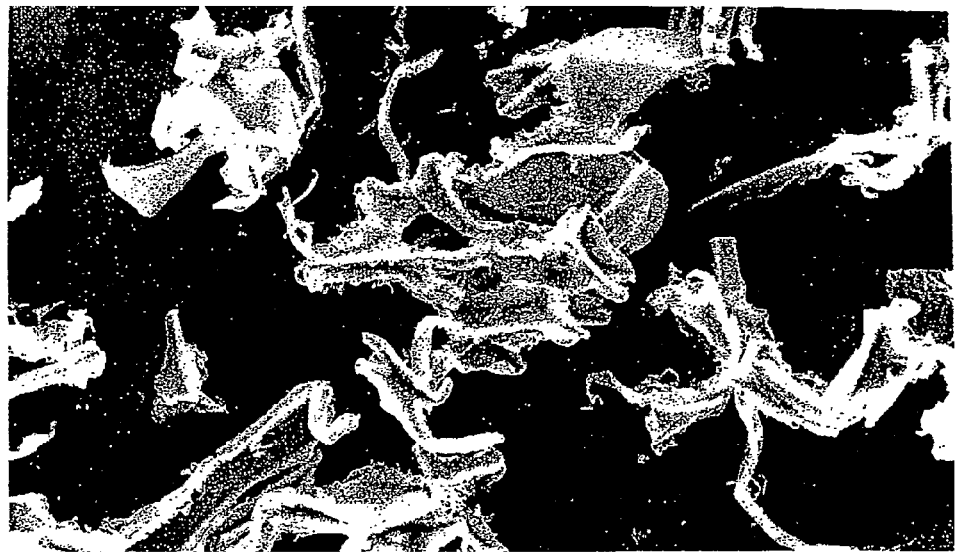

The individual gelatine or collagen particles may be spherical or non-spherical, such as "rod-like" or "flake-like" and they may be "curved" as can be seen on FIGS. 1A and 1B. However, independently of the actual physical form of the particles, a requirement of the particles is that they should exhibit excellent flowability properties or expressed differently, the particles should not be too cohesive. Flowability may, for example, be expressed in terms of flow rate (g/sec) and may be measured in a standardised funnel as described Ph. Eur. using a specified aperture diameter. Alternatively, cohesion may be measured in a Powder Flow Analyser as described by Freeman in *Pharmaceutical Technology Europe*, January 2004, pp. 41-43. Preferably, the cohesion index, when measured by the above-mentioned Powder Flow Analyser method is at the most 150, such as at the most 140, e.g. at the most 130, more preferably at the most 120, such as at the most 110, in particular at the most 100, such as at the most 90, e.g. at the most 80, at the most 70, at the most 60 or at the most 50.

Furthermore, the gelatine or collagen particles described herein must have a suitable density. When used herein, the term "density" refers to either "poured density", "tapped density" or "particle density" as defined in Ph. Eur. On the one hand, the density of the particles should not be too low as the particles would then have a tendency to dust upon application to the wound area. On the other hand, the density should not be too high as the flowability properties would then not be satisfactory. Accordingly, the gelatine or collagen powder preferably has a poured density in the range of 0.05-0.3 g/ml, such as in the range of 0.06-0.25 g/ml, e.g. in the range of 0.07-0.20 g/ml, more preferably in the range of 0.075-0.15 g/ml. Similarly, the gelatine or collagen powder preferably has a tapped density in the range of 0.075-0.4 g/ml, such as in the range of 0.1-0.3 g/ml, e.g. in the range of 0.125-0.25 g/ml, more preferably in the range of 0.15-0.25 g/ml.

Gelatine or Collagen Powder in Dry Form

The composition described herein will normally be in dry form. Accordingly, in a preferred embodiment of the invention the delivery system contains a composition comprising dry gelatine or collagen powder.

In the present context the term "dry" when used in connection with the terms "powder" or "particle" means that no liquid substances, such as liquid water, organic solvents, etc., are present in the gelatine or collagen powder composition. Accordingly, compositions which are in the form of solutions, dispersions, suspensions, gels, pastes, and the like are not encompassed by the terms "dry powder" or "dry particle". The powder composition may, however, have a certain moisture content provided that the flowability properties of the powder is not adversely affected. Typically, the water (moisture) content of the powder is at the most 20% (w/w), such as at the most 18% (w/w), preferably at the most 16% (w/w), such as at the most 15% (w/w), more preferably at the most 14% (w/w), such as the most 13% (w/w), in particular at the most 12% (w/w), such as at the most 11% (w/w).

As will be understood, once the composition is sprayed onto the wound area it is critical that the powder adheres to the application site, i.e. the composition must be sufficiently tacky to adhere to the wound area. Accordingly, in an interesting embodiment of the invention the composition further comprises an agent, which improves the adhesive properties of the composition. As the composition is typically applied to the wound area and hence may enter the blood stream of the patient, it is of utmost importance that the above-mentioned agent is biocompatible, i.e. non-toxic to an animal, such as a human being, when/if entering the blood stream or being in long-term contact with human tissue. In other words, the term "biocompatible" means that the agent in question has the capability to coexist with living tissues or organisms without causing harm, i.e. without giving rise to adverse side-effects.

Suitable agents, which may improve the adhesive properties (or the tackiness) of the composition are well-known to the person skilled in the art. One class of suitable agents include saccharides, such as monosaccharides, disaccharides, oligosaccharides, polysaccharides, and combinations thereof.

When used herein the term "saccharide", as well as the terms "monosaccharide", "disaccharide", "oligosaccharide" and "polysaccharide", also encompasses derivatives thereof, such as saccharides comprising one or more aminosugar units. In the present context, an aminosugar unit is a sugar unit wherein at least one of the hydroxy groups available in the sugar unit has been substituted by an amino group or an alkanoylated amino group such as an acetylated amino group. Accordingly, it will be understood that saccharides containing one or more glucosamine and/or N-acetylglucosamine unit(s) are also encompassed by the above-mentioned terms. Apart from the aminosugar units, the saccharide may contain unsubstituted sugar units or sugar units substituted with e.g. alkoxy (such as 2,3-dimethylglucose) or acyloxy.

Specific examples of monosaccharides include glucose, mannose, fructose, threose, gulose, arabinose, ribose, erythrose, lyxose, galactose, sorbose, altrose, tallose, idose, rhamnose, allose, and derivatives thereof, e.g. pentosamines, hexosamines, such as glucosamine or N-acetylglucosamine, and glucoronic acid. In particular glucose is preferred.

Specific examples of disaccharides include sucrose, maltose, lactose, cellubiose as well as derivatives thereof. In particular sucrose is preferred.

Specific examples of polysaccharides include glycogen, chitin, chitosan, starch such as potato starch, as well as combinations thereof. Specific examples of polysaccharide derivatives include glycosaminoglycans such as chondroitin, chondroitin sulfate, hyaluronic acid, dermatan sulfate and keratan sulfate; aminated dextrans including DEAE-dextran; aminated starch, aminated glycogen, aminated cellulose, aminated pectin, and salts, complexes, derivatives and mixtures thereof.

In an interesting embodiment of the invention, the composition further comprises an agent which improves the adhesive properties of said composition, where said agent is selected from the group consisting of glucose, sucrose, and a mixture thereof.

Other examples of agents which improve the adhesive properties of the composition include hydrocarbon resins, rosin resins and terpene resins. Hydrocarbon resins are commercially available under the tradenames Escorez® from ExxonMobil; Regalite®, Piccotac® and Picco® from Eastman; Indopol® from BP or Arkon®. Examples of rosin esters include esters of hydrogenated wood rosin e.g. pentaerythritol ester of hydrogenated wood rosin, esters of partially hydrogenated wood rosin e.g. pentaerythritol esters of partially hydrogenated wood rosin, esters of wood rosin, esters of modified wood rosin, esters of partially dimerized rosin, esters of tall oil rosin, esters of dimerized rosin, and similar rosins, and combinations and mixtures thereof. Such rosin esters are commercially available under the tradenames Foral®, Foralyn®, Pentalyn®, Permalyn® and Staybelite®.

Further examples of agents which improve the adhesive properties of the composition include Gum Karaya, sometimes known as Sterculia gum, Gum Arabicum, Gum Karrageenan, celluloseethers, such as sodium carboxymethylcellulose, Manuba Honey, casein, alginates or fatty acid esters, such as the fatty acid esters disclosed in WO 95/26715.

Thus, in an interesting embodiment of the invention, the composition comprises at least one agent which improves the adhesive properties of the composition. Evidently, the exact amount of agent may vary depending on what specific agent is being used, but the composition typically comprises 0.1-50% (w/w) of the agent, based on the total weight of the composition. Preferably, and in particular when the agent which improves the adhesive properties of the composition is a saccharide, the composition comprises 1-25% (w/w), such as 5-20% (w/w), e.g. 5-15% (w/w), 5-10% (w/w), or 10-15% (w/w), based on the total weight of the composition.

The agent may be applied to the composition by methods well-known to the person skilled in the art. For example, the agent may be in admixture with the gelatine or collagen powder and/or the agent may be coated on the surface of the gelatine or collagen powder. The composition may contain additional substances, such as coagulation factors, antifibrinolytic agents, surfactants, growth factors to promote healing, antimicrobial agents, calcium ions to aid coagulation, adrenaline or other substances capable of constricting blood vessels.

Specific examples of coagulation factors include coagulation factors selected from the group consisting of thrombin, fibrinogen, aprotinin, fibronectin, factor XIII, factor VII, factor VIII, and combinations thereof. Such compounds may be of any mammalian origin, such as of porcine or human origin, or may be obtained by recombinant means by methods well-known to the skilled person. It will be understood that gelatine and collagen are not considered as being coagulation factors.

Antifibrinolytic agents may be selected from the group consisting of tranexamic acid, ε-aminocaproic acid, aprotinin, pepstatin, leupeptin, antipain, chymostatin, gabexate, and mixtures thereof. If present, the antifibrinolytic agent is preferably tranexamic acid.

Antimicrobial agents may be selected from bactericidal or bacteriostatic agents, such as antibiotics and sulphonamides, antiviral compounds, antimycotic agents and anti-infectives. Antibiotics may be selected from e.g. β-lactams, penicillins, cephalosporins, monobactams, macrolides, polymyxins, tetracyclines, chloramphenicol, thrimethoprim, aminoglycosides, clindamycin, and metronidazole; sulphonamides may as an example be selected from sulphadimidine or sulphadimethoxin; antimycotic agents may be selected from amphotericin B, ketoconazol and miconazol; and antiviral agent from idoxuridine andazidothymidin. Suitable antiinfectives may as an example be selected from halogens, chlorohexidine and quarternary ammonium compounds. Other examples of bactericidal or bacteriostatic compounds include silver ions, in particular in the form of silver ion complexes.

Surfactants may be selected from the group consisting of anionic surfactants, cationic surfactants, non-ionic surfactants and surface active biological modifiers.

Examples of anionic surfactants include surfactants selected from the group consisting of potassium laurate, triethanolamine stearate, sodium lauryl sulfate, sodium dodecylsulfate, alkyl polyoxyethylene sulfates, sodium alginate, dioctyl sodium sulfosuccinate, phosphatidyl glycerol, phosphatidyl inositol, phosphatidylserine, phosphatidic acid and their salts, glyceryl esters, sodium carboxymethylcellulose, bile acids and their salts, cholic acid, deoxycholic acid, glycocholic acid, taurocholic acid, glycodeoxycholic acid, and calcium carboxymethylcellulose. In particular sodium lauryl sulfate is preferred.

Examples of cationic surfactants include surfactants selected from the group consisting of quaternary ammonium compounds, benzalkonium chloride, cetyltrimethylammonium bromide, chitosans and lauryldimethylbenzylammonium chloride.

Examples of non-ionic surfactants include surfactants selected from the group consisting of polyoxyethylene fatty alcohol ethers, polyoxyethylene sorbitan fatty acid esters, polyoxyethylene fatty acid esters, sorbitan esters, polyoxyethylene sorbitan esters (such as Tween 80), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers, polaxamines, methylcellulose, hydroxycellulose, hydroxy propylcellulose, hydroxy propylmethylcellulose, noncrystalline cellulose, polysaccharides, starch, starch derivatives, hydroxyethylstarch, polyvinyl alcohol, and polyvinylpyrrolidone.

Examples of surface active biological modifiers include, e.g., albumin and casein.

However, in a preferred embodiment of the invention, the composition does not contain such additional substances, i.e. said composition does not contain coagulation factors, antifibrinolytic agents, surfactants and/or antimicrobial agents.

In one interesting embodiment of the invention the preparation comprises an agent that is incompatible with moisture and/or water. The embodiment might comprise both a dry powder and a liquid to be combined with the powder to form a paste immediately before use. In such an embodiment the dry powder and the liquid is kept separate under storage. The dry component and the liquid component might be contained in the same packaging while still kept without contact under storage. The agent incompatible with moisture and/or water can be an antimicrobial agents, a polysaccharide or a protein. The composition is in dry form under storage to improve stability. The composition can be contacted with water immediately before use.

Sponges of gelatine or collagen, in particular hardened sponges of gelatine (such as the commercially available Spongostan® sponges and Surgifoam® sponges) or collagen may be micronised by methods well known in the art. Thus, the compositions described herein may, e.g., be prepared by any suitable micronisation technique known to the skilled person, such as rotary bed, extrusion, granulation and treatment in an intensive mixer, milling (e.g. by using a hammer mill or a centrifugal mill), or spray drying.

The gelatine or collagen powder composition is preferably subjected to a sterilisation treatment by application of radiation, such as β-radiation. The dose typically lies in the range of 20-60 kGy, e.g. 25 kGy.

As indicated above, the gelatine and/or collagen powder compositions described herein may be used as a medicament. Accordingly, in a further aspect the present invention relates to a method of promoting haemostasis in a patient in need thereof, said method comprising spraying a composition as defined herein onto at least a portion of the area where bleeding occurs. In a still further aspect the present invention relates to the use of gelatine or collagen powder having a mean particle size of at least 10 µm for the manufacture of a composition as defined herein for promoting haemostasis, wherein said composition is sprayed onto at least a portion of the area where bleeding occurs.

The powder composition may be applied directly to surfaces and optionally, after being applied to the surface, held in place by pressure, e.g. by means of sponges, pads, dressings, webs, films, etc. or by other materials normally used in the medical practice. A preferred material for holding the composition in place after being applied to the wound area is surgical gauze or cotton gauze, optionally wetted in saline.

The powder delivery system of the invention may be used in an array of surgical procedures wherein bleeding control is desired, such as in orthopedic precedures, e.g. in connection with laminectomy, total hip replacement and hip revisions, knee surgery, spinal fusion, etc.; in cardiothoracic/cardiovascular procedures, such as in connection with CABGs, valve replacements, aotic surgery, abdominal aortic aneurisms, carotid endarterectomy and femoral-popliteal bypass, amongst others.

Gelatine or Collagen in the Form of a Gel

In another interesting embodiment of the invention the composition is in the form of a gel.

The term "gel" may be used interchangeable with words like "paste", "suspension" and the like. In the present context, the term "gel" refers to a solid or semi-solid disperse system wherein a solid material is dispersed in a liquid medium. The solid material may also be referred to as a gel-forming agent. Furthermore, a gel is characterised by having a dynamic viscosity above that of water.

As will be understood the solid material (or the gel-forming agent) of the gel is the gelatine particles or the collagen particles disclosed herein. Alternatively, the solid material may be a mixture of the gelatine and collagen particles disclosed herein.

The gel may be obtained by suspending the gelatine or collagen particles described herein in a liquid medium, in particular in an aqueous medium. Typically, about 1-20 ml liquid medium is employed per gram gelatine or collagen, preferably 2-18 ml/g, such as 3-16 ml/g, e.g. 4-14 ml/g, more preferably 6-14 ml/g, in particular 8-12 ml/g.

As mentioned above, the liquid medium is preferably an aqueous medium. More preferably the aqueous medium contains salts, such as sodium chloride, dissolved therein. Most preferably, the aqueous medium is saline.

As will be understood, once the composition is applied onto the wound area it is critical that the composition adheres to the application site, i.e. the composition must be sufficiently tacky to adhere to the wound area. Accordingly, in an interesting embodiment of the invention the composition further comprises an agent, which improves the adhesive properties of the composition. As the composition is typically applied to the wound area and hence may enter the blood stream of the patient, it is of utmost importance that the above-mentioned agent is biocompatible, i.e. non-toxic to an animal, such as a human being, when/if entering the blood stream or being in long-term contact with human tissue. In other words, the term "biocompatible" means that the agent in question has the capability to coexist with living tissues or organisms without causing harm, i.e. without giving rise to adverse side-effects.

Suitable agents, which may improve the adhesive properties (or the tackiness) of the composition are well-known to the person skilled in the art. One class of suitable agents include saccharides, such as monosaccharides, disaccharides, oligosaccharides, polysaccharides, and combinations thereof.

When used herein the term "saccharide", as well as the terms "monosaccharide", "disaccharide", "oligosaccharide" and "polysaccharide", also encompasses derivatives thereof, such as saccharides comprising one or more aminosugar units. In the present context, an aminosugar unit is a sugar unit wherein at least one of the hydroxy groups available in the sugar unit has been substituted by an amino group or an alkanoylated amino group such as an acetylated amino group. Accordingly, it will be understood that saccharides containing one or more glucosamine and/or N-acetylglucosamine unit(s) are also encompassed by the above-mentioned terms. Apart from the aminosugar units, the saccharide may contain unsubstituted sugar units or sugar units substituted with e.g. alkoxy (such as 2,3-dimethylglucose) or acyloxy.

Specific examples of monosaccharides include glucose, mannose, fructose, threose, gulose, arabinose, ribose, erythrose, lyxose, galactose, sorbose, altrose, tallose, idose, rhamnose, allose, and derivatives thereof, e.g. pentosamines, hexosamines, such as glucosamine or N-acetylglucosamine, and glucoronic acid. In particular glucose is preferred.

Specific examples of disaccharides include sucrose, maltose, lactose, cellubiose as well as derivatives thereof. In particular sucrose is preferred.

Specific examples of polysaccharides include glycogen, chitin, chitosan, starch such as potato starch, as well as combinations thereof. Specific examples of polysaccharide derivatives include glycosaminoglycans such as chondroitin, chondroitin sulfate, hyaluronic acid, dermatan sulfate and keratan sulfate; aminated dextrans including DEAE-dextran; aminated starch, aminated glycogen, aminated cellulose, aminated pectin, and salts, complexes, derivatives and mixtures thereof.

In an interesting embodiment of the invention, the composition further comprises an agent which improves the adhesive properties of said composition, where said agent is selected from the group consisting of glucose, sucrose, hyaluronic acid, sodium hyaluronate and a mixture thereof.

Other examples of agents which improve the adhesive properties of the composition include hydrocarbon resins, rosin resins and terpene resins. Hydrocarbon resins are commercially available under the tradenames Escorez® from ExxonMobil; Regalite®, Piccotac® and Picco® from Eastman; Indopol® from BP or Arkon®. Examples of rosin esters include esters of hydrogenated wood rosin e.g. pentaerythritol ester of hydrogenated wood rosin, esters of partially hydrogenated wood rosin e.g. pentaerythritol esters of partially hydrogenated wood rosin, esters of wood rosin, esters of modified wood rosin, esters of partially dimerized rosin, esters of tall oil rosin, esters of dimerized rosin, and similar rosins, and combinations and mixtures thereof. Such rosin esters are commercially available under the tradenames Foral®, Foralyn®, Pentalyn®, Permalyn® and Staybelite®.

Further examples of agents which improve the adhesive properties of the composition include Gum Karaya, sometimes known as Sterculia gum, Gum Arabicum, Gum Karrageenan, celluloseethers, such as sodium carboxymethylcellulose, Manuba Honey, casein, alginates or fatty acid esters, such as the fatty acid esters disclosed in WO 95/26715.

The composition may contain additional substances, such as coagulation factors, antifibrinolytic agents, surfactants, preservatives, solubilising agents, growth factors to promote healing, antimicrobial agents, calcium ions to aid coagulation, adrenaline or other substances capable of constricting blood vessels.

Specific examples of coagulation factors include coagulation factors selected from the group consisting of thrombin, fibrinogen, aprotinin, fibronectin, factor XIII, factor VII, factor VIII, and combinations thereof. Such compounds may be of any mammalian origin, such as of porcine or human origin, or may be obtained by recombinant means by methods well-known to the skilled person. It will be understood that gelatine and collagen are not considered as being coagulation factors.

Antifibrinolytic agents may be selected from the group consisting of tranexamic acid, $\epsilon$-aminocaproic acid, aprotinin, pepstatin, leupeptin, antipain, chymostatin, gabexate, and mixtures thereof. If present, the antifibrinolytic agent is preferably tranexamic acid.

Antimicrobial agents may be selected from bactericidal or bacteriostatic agents, such as antibiotics and sulphonamides, antiviral compounds, antimycotic agents and anti-infectives. Antibiotics may be selected from e.g. $\beta$-lactams, penicillins, cephalosporins, monobactams, macrolides, polymyxins, tetracyclines, chloramphenicol, thrimethoprim, aminoglycosides, clindamycin, and metronidazole; sulphonamides may as an example be selected from sulphadimidine or sulphadimethoxin; antimycotic agents may be selected from amphotericin B, ketoconazol and miconazol; and antiviral agent from idoxuridine and azidothymidin. Suitable antiinfectives may as an example be selected from halogens, chlorohexidine and quaternary ammonium compounds. Other examples of bactericidal or bacteriostatic compounds include silver ions, in particular in the form of silver ion complexes.

Surfactants may be selected from the group consisting of anionic surfactants, cationic surfactants, non-ionic surfactants and surface active biological modifiers.

Examples of anionic surfactants include surfactants selected from the group consisting of potassium laurate, triethanolamine stearate, sodium lauryl sulfate, sodium dodecylsulfate, alkyl polyoxyethylene sulfates, sodium alginate, dioctyl sodium sulfosuccinate, phosphatidyl glycerol, phosphatidyl inositol, phosphatidylserine, phosphatidic acid and their salts, glyceryl esters, sodium carboxymethylcellulose, bile acids and their salts, cholic acid, deoxycholic acid, glycocholic acid, taurocholic acid, glycodeoxycholic acid, and calcium carboxymethylcellulose. In particular sodium lauryl sulfate is preferred.

Examples of cationic surfactants include surfactants selected from the group consisting of quaternary ammonium compounds, benzalkonium chloride, cetyltrimethylammonium bromide, chitosans and lauryidimethylbenzylammonium chloride.

Examples of non-ionic surfactants include surfactants selected from the group consisting of polyoxyethylene fatty alcohol ethers, polyoxyethylene sorbitan fatty acid esters, polyoxyethylene fatty acid esters, sorbitan esters, polyoxyethylene sorbitan esters (such as Tween 80), glycerol monostearate, polyethylene glycols, polypropylene glycols, cetyl alcohol, cetostearyl alcohol, stearyl alcohol, aryl alkyl polyether alcohols, polyoxyethylene -polyoxypropylene copolymers, polaxamines, methylcellulose, hydroxycellulose, hydroxy propylcellulose, hydroxy propylmethylcellulose, noncrystalline cellulose, polysaccharides, starch, starch derivatives, hydroxyethylstarch, polyvinyl alcohol, and polyvinylpyrrolidone.

Examples of surface active biological modifiers include, e.g., albumin and casein.

Examples of preservatives include benzoic acid, sorbic acid, parabens (e.g. methyl-p-hydroxy benzoic acid, ethyl-p-hydroxy benzoic acid, propyl-p-hydroxy benzoic acid, butyl-p-hydroxy benzoic acid and mixtures thereof), benzyl alcohol, chlorhexidine or benzalkonium chloride.

Specific examples of solubilising agents include water-miscible organic compounds such as glycerol or propylene glycol.

Such gel or gel-like compositions may be applied to the wound area in a manner well-known to the person skilled in the art.

Delivery System for Powder Compositions

The powder delivery system is preferably a hand-held delivery system, which may be used, for example, by surgeons during operations to arrest bleedings.

A suitable powder delivery system comprises a chamber storing a powdered composition, such as a composition comprising gelatine or collagen powder having a mean particle size of at least 10 µm. The delivery system further contains at least one discharge opening sized for distributing the composition. The discharge opening should preferably be sized for distributing the composition to a surface, such as a wound, skin, an organ, etc., in controlled amounts, in particular so that the risk of overdosing is avoided.

The delivery system may be a simple salt shaker-like device. However, in a preferred embodiment the device comprises an elongate tip for distribution of the composition, whereby it is possible more accurately and faster to apply the composition at the right place on a bleeding area and further in confined space regions. The tip can be interchangeable so that the most suitable tip can be selected for the specific application of the composition. The tip opening typically has a diameter of from 0.05-5 mm, preferably of from 0.05-4 mm, such as of from 0.05-3 mm, e.g. of from 0.075-2.5 mm, such as about 1 mm, about 1.5 mm or about 2.0 mm.

The delivery system may be powered and e.g. comprise an electric motor rotating a plate with holes to register with corresponding holes at the discharge opening. However, in a preferred embodiment the delivery system is manually operable, such as by shaking or squeezing the system, thereby keeping the cost and complexity of the system at a minimum.

Alternatively or additionally the delivery system may comprise a resilient wall portion or bellows, such that the resilient wall portion or bellows may be compressed to expel the composition from the chamber through the discharge opening. This is a cost effective and simple embodiment, which further is intuitive and easy to use. Additionally, the composition may be discharged to the surface very precisely, as the discharge opening is kept steady.

As will be evident to the skilled person, the delivery system may comprise some kind of powered mechanism to compress the resilient wall portion or bellows. In a preferred embodiment, however, the resilient wall portion or bellows is adapted to be manually activated, such as by finger pressure, to discharge at least part of the composition.

The delivery system can be manufactured in a conventional way, which will be known to the person skilled in the art. The system is preferably made of one or more suitable plastic materials, such as polypropylene and/or polyethylene. The dimensions of the system may vary depending on the actual design. It is important, however, that the system should still be manually operable by one hand. Typically, a total amount of 0.5-5 g, such as 1-3 g of the powder composition is loaded into the delivery system.

In a particular preferred embodiment of the invention, the delivery system may further comprise a protective structure arranged at the discharge opening. What is achieved is that the discharge opening is, at least to some extent, isolated from the surroundings. This, in turn, is advantageous when the delivery system is used in connection with surgery where contamination and, in particular, clogging of the discharge opening due to blood coagulation, may then be minimised or completely avoided.

The protective structure may be constructed in various ways. The protective structure may surround the discharge opening but have a relative open structure as show in FIG. 4. Alternatively, the protective structure may surround the discharge opening and be in the form of a grid. In a preferred embodiment the protective structure is a skirt portion arranged to extend from the discharge opening.

The protective structure may be made from the same material as the delivery system, and the protective structure may form an integral part of the delivery system or it may be a non-integral part, such as a removable part, of the delivery system.

Since a delivery system comprising a protective structure as described above is believed to be novel and inventive per se, the present invention also relates to a powder delivery system containing a chamber for storing a powder composition, said chamber comprising at least one discharge opening sized for distributing said composition and a protective structure arranged at the discharge opening.

It will be understood that said delivery system preferably contains a gelatine or collagen powder composition as described hereinbefore. However, the delivery system may contain any powder composition suitable for haemostatic purposes.

Examples of specific materials useful in the practice of the present invention comprise materials from within the classes of polysaccharides, cellulosics, polymers (natural and synthetic), inorganic oxides, ceramics, zeolites, glasses, metals, and composites. Preferred materials are of course non-toxic and are provided as a sterile supply. The particulate polysaccharides may be provided as starch, cellulose and/or pectins, and even chitin may be used (animal sourced from shrimp, crab and lobster, for example). Glycosaccharides or glycoconjugates which are described as associations of the saccharides with either proteins (forming glycoproteins, especially glycolectins) or with a lipid (glycolipid) are also useful. These glycoconjugates appear as oligomeric glycoproteins in cellular membranes.

Ceramic materials may be provided from the sintering, or sol-gel condensation or dehydration of colloidal dispersions of inorganic oxides such as silica, titanium dioxide, zirconium oxide, zinc oxide, tin oxide, iron oxide, cesium oxide, aluminum oxide and oxides of other metal, alkaline earth, transition, or semimetallic chemical elements, and mixtures thereof. By selection of the initial dispersion size or sol size of the inorganic oxide particles, the rate of dehydration, the temperature at which the dehydration occurs, the shear rate within the composition, and the duration of the dehydration, the porosity of the particles and their size can be readily controlled according the skill of the ordinary artisan.

With regard to cellulosic particles, natural celluloses or synthetic celluloses (including cellulose acetate, cellulose butyrate, cellulose propionate, oxidised cellulase and salts thereof, in particular calcium salts thereof) as well as fibers and microfibers of cellulose-based materials may be used in accordance with the invention.

It will be understood that where the materials, whether of cellulose or other compositions, have a size which may be too large for a particular application, the particles may be ground or milled to an appropriate size. This can be done by direct mortar and pestle milling, ball milling, crushing (as long as the forces do not compress out all of the porosity), fluidised bed deaggregation and size reduction, and any other available physical process.

Figure 2:
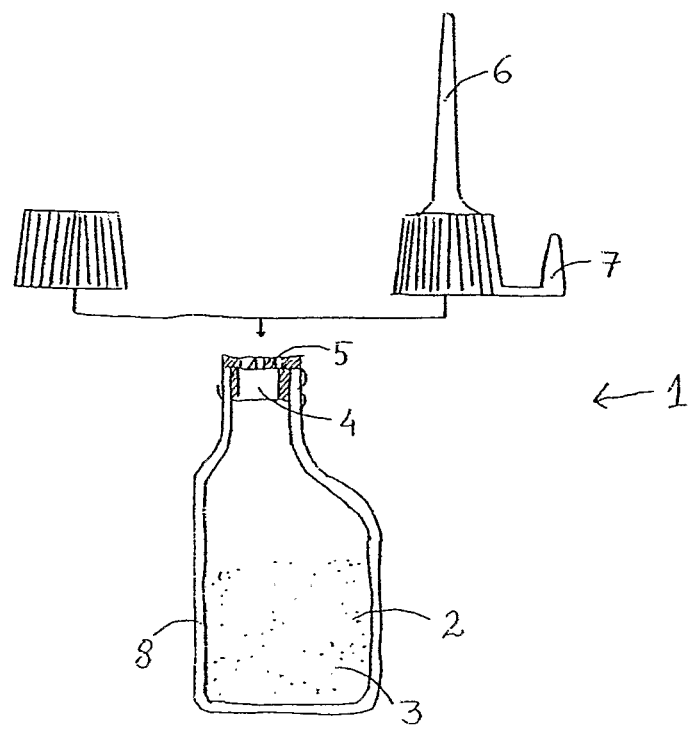

A particularly interesting and commercially available material comprises polysaccharide beads, such as dextran beads which are available as Sephadex®. beads from Pharmacia Labs. These are normally used in surgery as an aid to debridement of surfaces to help in the removal of damaged tissue and scar tissue from closed wounds. In the following the device will be more thoroughly explained with reference to the drawings in which:

FIG. 2 is a sketch of a powder delivery system according to the invention.

Figure 3:
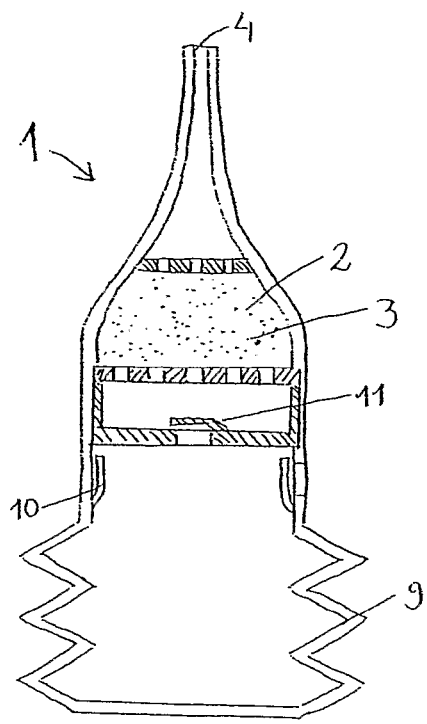

FIG. 3 is an alternative embodiment of the delivery system.

Figure 4:
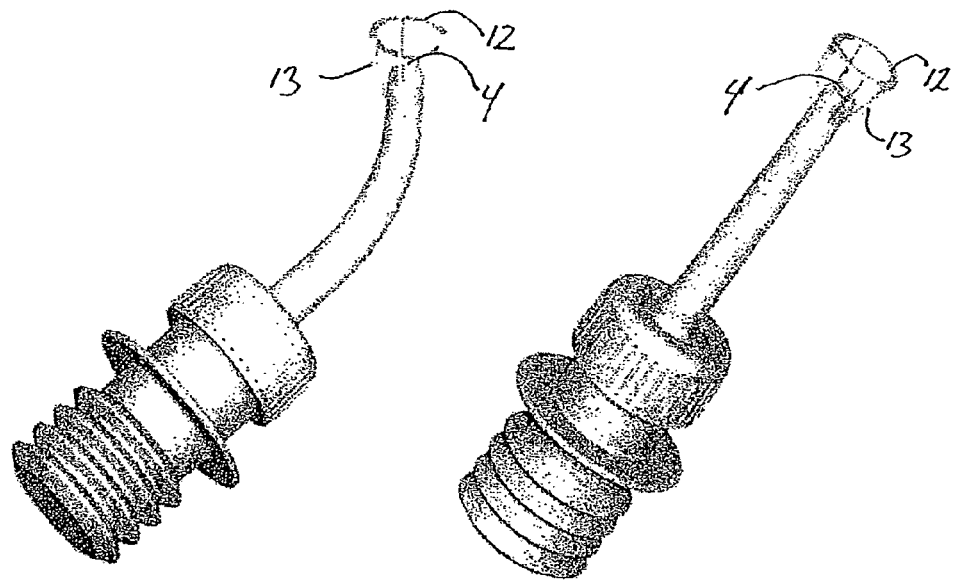

FIG. 4 is a sketch of a protective structure for the delivery system.

FIG. 2 schematically illustrates a simple embodiment of the delivery system according to the invention. The delivery system (1) comprises a chamber (2) storing a composition (3) comprising gelatine or collagen powder, and the chamber (2) has at least one discharge opening (4). The shown delivery system (1) further comprises a plug with sift (5). As will be appreciated by the skilled person the composition (3) in the chamber (2) may be distributed by turning the delivery system up-side-down and if necessary or convenient shaking the system. The composition (3) will then leave the chamber (2) through the discharge opening (4) and the sift (5) by influence of gravity. As shown, the delivery system may further be equipped with an extended nozzle or elongate tip (6) which may further be provided with a reclosure cap (7). The chamber (2) may have walls (8) of a resilient or flexible material, such as plastic, so it is possible to squeeze the walls (8) inwardly forcing the composition (3) out of the chamber (2), e.g. with the fingers of one hand only.

An alternative embodiment of the delivery system 1 is shown in FIG. 3. The delivery system (1) comprises a chamber (2) comprising a composition (3), and a bellows (9) which when squeezed generates air pressure forcing air through the chamber (2) and driving composition (3) into the extended nozzle and out through the discharge opening (4). The delivery system (1) may be provided with a one-way inlet valve (10) as shown to let air enter the bellows (9) from the outside. The delivery system (1) may further be provided with a one-way outlet valve (11) to ensure that powder is not sucked into the bellows (9).

A special distance protective structure is illustrated in FIG. 4. The embodiment shown comprises a ring (12) supported by legs (13), so the discharge opening (4) of the extended nozzle cannot abut a surface. Alternatively, the protective structure may be a skirt (not shown) attached to the discharge opening (4), said skirt extending in front of the discharge opening (4) of the extended nozzle.

A further aspect of the delivery system is in the form of a pen-like device. This pen-like device is a device suitable for pressurised delivery of an agent wherein the delivery is through an outlet of a hollowed member upon compression of a bow engaged with a serrated edge portion of a serrated piston located within the hollowed membrane, so as to propel the piston in the direction of the outlet, said engagement being through an aperture in said hollowed tubular membrane. Compression of the engaged bow propels the piston in the direction of the outlet by a distance defined by the radius of the bow so as to deliver the agent. Release of the compression allows for the bow to return to its curved position of higher potential energy and to re-engage with a second serrated edge portion of the piston, said second serrated edge portion being distally positioned on the piston from the outlet.

As stated, the delivery is made in finite volumes defined by the radius of the bow in concert with the spacing of the serrated edges. The degree of compression can be so as to project the serrated piston by a distance of 1-4 serrations, such as 1, 2, 3, or 4 preferably 1, 2 and 3 serrations, more preferably 1 and 2 serrations. For instance, full compression propels the piston a distance of 2 serrations and slight compression propels the piston by a distance of 1 serration. In order for the bow to return to its position of maximal potential energy, it's resting position, it must re-engaged with a serration distally located on the piston from the outlet.

The hollowed member may be a hollowed tubular member with an inner diameter appropriate and suitable for the agent to be delivered. The agent may be in an array of forms such as in the form of a liquid, solid granules, powder, paste, suspension or emulsion.

In a typical embodiment, the radius of the bow is such that compression of its arch results in the projection of the serrated piston so as to deliver a volume of 0.05 to 2 ml per full compression, typically 0.075 to 1 ml, more typically 0.1 to 0.5 ml, such as 0.1, 0.2, 0.3, 0.4 and 0.5 ml.

The present inventors have found that the delivery is of a high pressure compared to conventional devices, and suitable for delivery of a powdered agent at a pressure of 50-200 N, such as 75-200 N, typically 100-180 N.

Figure 8:
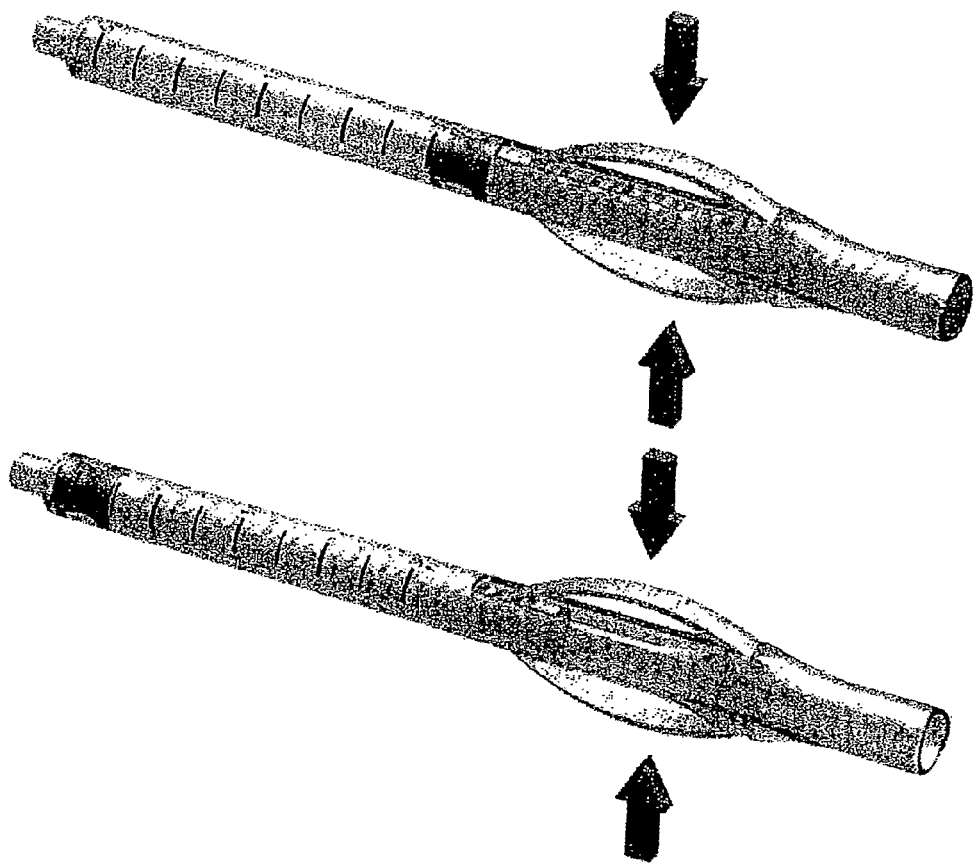

The bow of the pen-like device is typically located along the longitudinal axis of the hollow member so as to render the device easy to hold and use at the same time, such as by compression by the thumb. FIG. 8 depicts an illustrative example of the pen-like device.

The invention is further illustrated by the following non-limiting examples.

EXAMPLES

Example 1A

Preparation of Micronised Gelatine Powder

The gelatine powder was produced on a Retsch Centrifugal Mill with a screen size of 80 μm using a speed of 10,000 rpm. Hardened and sterilised gelatine sponges (Spongostan®) were cut into pieces of 0.5 cm$^2$ and about 750 mg material was milled at a time (until the screen was full). After each milling round the screen was cooled and cleaned by means of a vacuum cleaner. The gelatine powder was subsequently sterilised by β-radiation (approximately 25 kGy).

A SEM picture of the obtained powder is shown in FIG. 1A (at 500 magnification).

Example 1B

Preparation of Micronised Gelatine Powder

The gelatine powder was produced on a Fitzpatrick Hammer Mill RP-M5A with a screen size of 74 μm using a speed of 4,500 rpm. Hardened and sterilised gelatine sponges (Spongostan®) were cut into pieces of 3×7 cm. After milling the gelatine powder was sterilised by β-radiation (approximately 25 kGy).

A SEM picture of the obtained powder is shown in FIG. 1B (at 500 magnification).

Example 2

Determination of Particle Size

Determination of the particle size distribution on the gelatine powder samples prepared in Examples 1A and 1B was performed by laser diffraction using the following equipment and settings:

| | |
|---|---|
| Laser diffraction | Malvern Mastersizer 2000 |
| Dispersion unit | Scirocco 2000 |
| Software version | Mastersizer 2000, version 4 |
| Sample amount | ~0.25 g |
| No. of measurements* | 3 |
| Disperser pressure | 1.0 bar |
| Feed opening | 10 mm |
| Feed rate | 80-95% |
| Obscuration | 2-6% |
| Obscuration filtering | Enabled |
| Measurements integrations | Minimum 4000 (4 seconds) |
| Calculation model | Fraunhofer |
| Sensitivity | Enhanced |
| Evaluation model | General purpose |

The result is calculated as an average result based on the light scattering patterns from each measurement. The average result is calculated using Malvern software.

Figure 5:
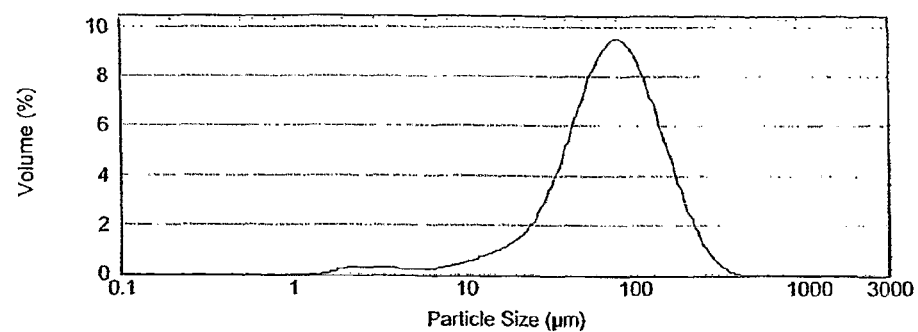
Figure 6:
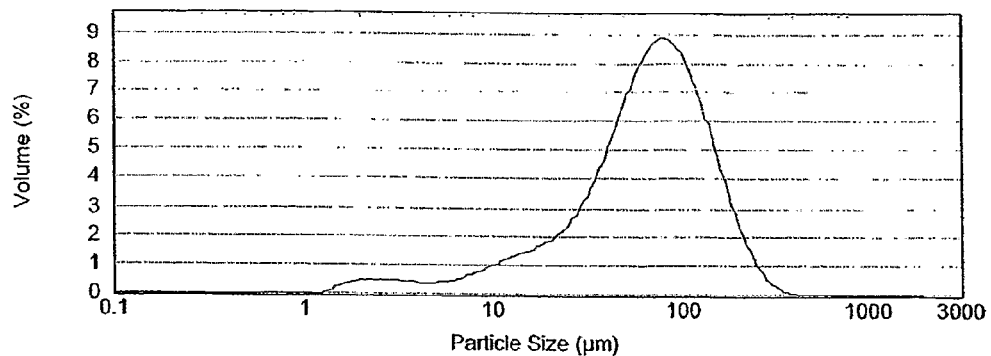

FIGS. 5 and 6 give a graphical representation of the particle size distribution. As can be seen, the mean particle size for both samples was about 80 μm.

The following percentiles of the volume size distribution of the two samples were found:

| Example 1A | |
|---|---|
| $D_{10\%}$ | 27.3 μm |
| $D_{50\%}$ | 74.5 μm |
| $D_{90\%}$ | 159.9 μm |
| Example 1B | |
| $D_{10\%}$ | 16.7 μm |
| $D_{50\%}$ | 68.6 μm |
| $D_{90\%}$ | 152.4 μm |

$D_{10\%}$, $D_{50\%}$, $D_{90\%}$ are the respective percentiles of the volume size distribution

Example 3

Determination of Water Content

Determination of the water content in the gelatine powder samples prepared in Examples 1A and 1B was performed by the "Loss On Drying" method described in Ph. Eur. Samples were analysed for 30 min. at 100° C. using a Mettler Infrarottrockner LP16. Data were collected every second minute.

The following water content in the two samples were found:

| Example 1A | 10.0% (w/w) |
|---|---|
| Example 1B | 8.0% (w/w) |

Example 4

Determination of Apparent and Particle Density

Determination of the apparent density (tapped density and poured density) of the gelatine powder samples prepared in Examples 1A and 1B was performed according to the methods described in Ph. Eur.

The following densities were found:

| Example 1A | |
|---|---|
| Tapped density | 0.23 g/ml |
| Poured density | 0.13 g/ml |
| Example 1B | |
| Tapped density | 0.17 g/ml |
| Poured density | 0.10 g/ml |

Determination of the particle density of the gelatine powder sample prepared in Example 1B was performed according to the pycnometric density method described in Ph. Eur.

| Particle density | 1.396 g/cm³ |
|---|---|

Example 5

Determination of Specific Surface Area

Determination of specific surface area of the gelatine powder samples prepared in Examples 1A and 1B was performed by nitrogen adsorption using the following conditions:

| Analytical equipment | Micromeritics Gemini 2375 BET (SN: 683) |
|---|---|
| Gas | Nitrogen (quality 5.0) |
| Relative pressure | 0.050-0.300 |
| Evacuation rate | 300.0 mmHg/min |
| Evacuation time | 5 minutes |
| Sample preparation | Dried for at least 24 h under vacuum at r.t. |

The following surface areas were found:

| Example 1A | |
|---|---|
| Specific surface area | 1.05 m²/g (1st measurement) |
| | 1.07 m²/g (2nd measurement) |
| | 1.06 m²/g (average) |
| Example 1B | |
| Specific surface area | 1.62 m²/g (1st measurement) |
| | 1.60 m²/g (2nd measurement) |
| | 1.61 m²/g (average) |

Example 6

Wetability and Saline Absorption

Wetability

Wetability was assessed under a macroscope while the wetting process took place. The conventionally used Surgifoam® Powder was compared with the powder according to the invention. Each of the powders was applied onto separate microscopic glass slides by means of a Vacuum Dispensing Unit to achieve a homogeneous layer of powder.

Parameters:
Macroscope: Meiji UniMac Zoom Macroscope
Light source: Schot KL1500 Electronic (level 3)
Two-armed light wire: Fibre Optic Eluminator (light from two sides)
Camera: Sony XC-75CE series no. 94154 (black/white)
Software: Piccolo Capture Driver version 1.6, MCM design The microscopic glass slide was placed under a macroscope and a picture was taken at the time-point of 0 seconds. After addition of a drop (35 μl) of saline, pictures were taken every 2 seconds. The zoom factor was 0.7 times enlargement and the objective was 2.5 times enlargement, resulting in a total of 1.75 times enlargement.

Figure 9:
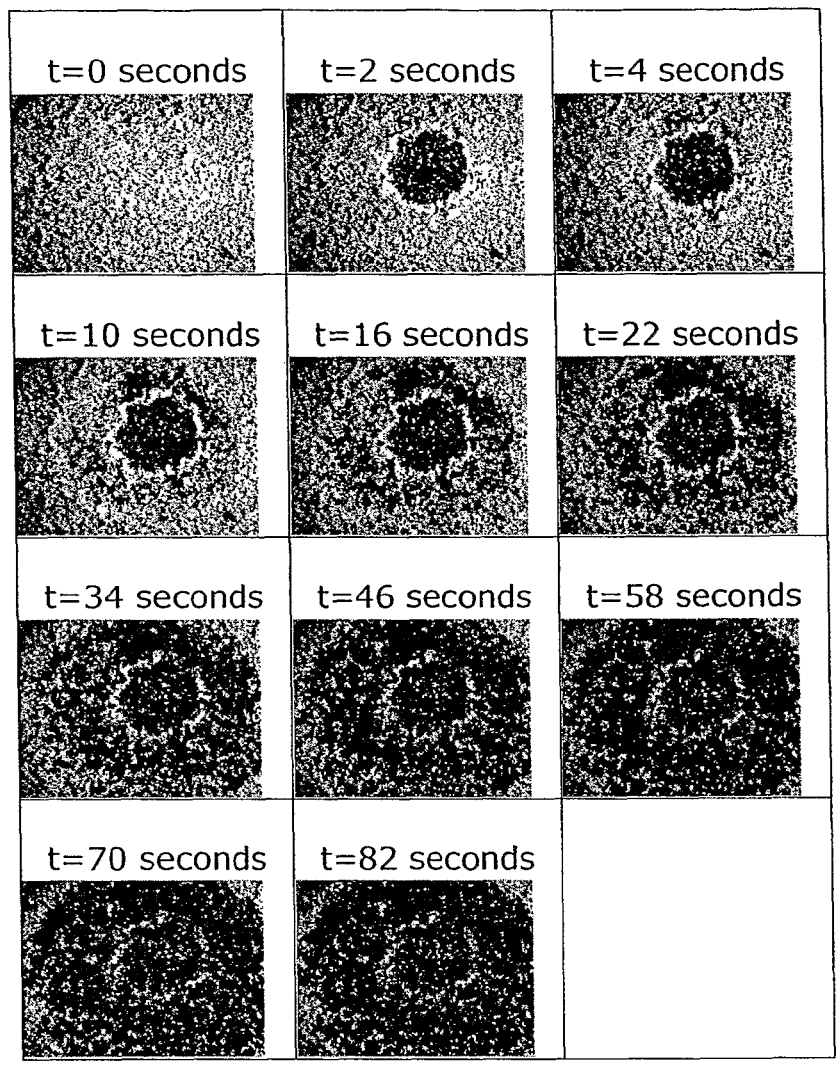
FIG. 9 illustrates a gelatine powder according to the present invention at time-points from 0 to 82 seconds after having a drop of saline applied on the surface. The illustrations are recorded according to the parameters described in Example 6.

FIG. 9 at the time-point of 0 seconds depicts the dry powder according to the invention before adding saline. At the time-point of 2 seconds a drop of saline is added to the powder. The saline droplet can be recognised as a dark zone to the time-point of 2 seconds. From the zone, where the droplet landed, it starts spreading out in a ring at 4 seconds. The ring continues to spread out, as is recognised at the following time-points. As the ring is spreading, the zone encircled by the spreading saline-droplet continuously becomes darker due to wetting of the powder.

Figure 10:
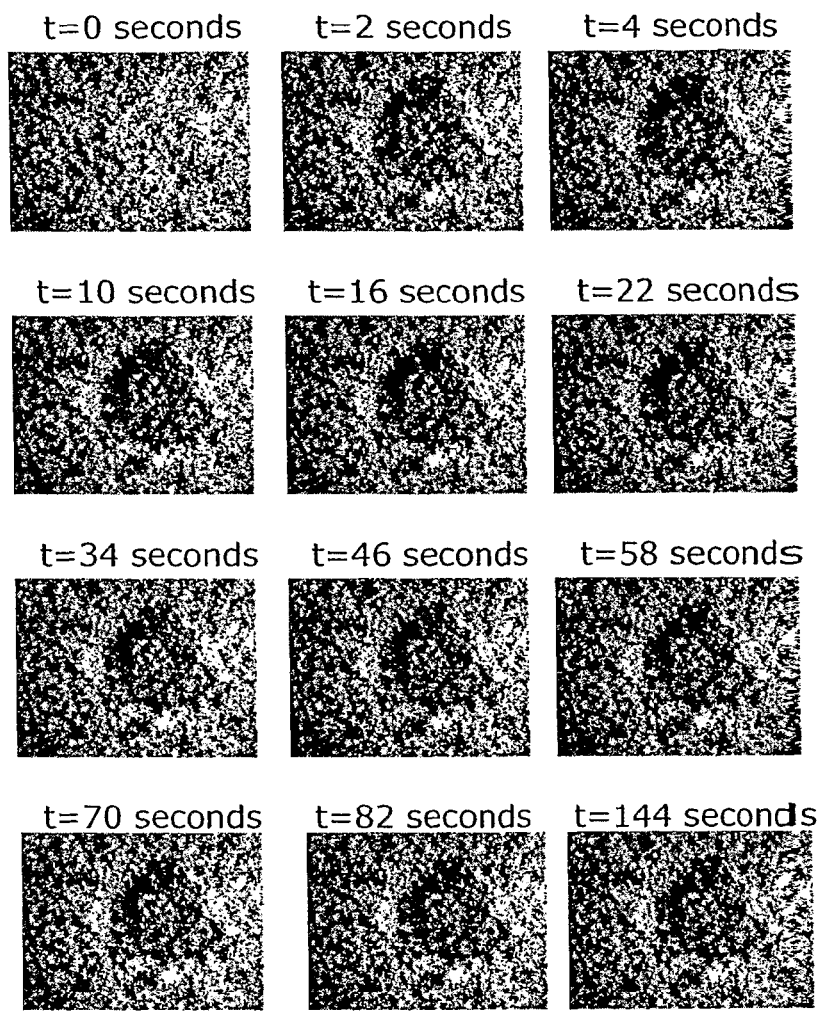
FIG. 10 illustrates a conventional gelatine powder (Surgifoam® Powder) at time-points from 0 to 144 second after having a drop of saline applied on the surface. The illustrations are recorded according to the parameters described in Example 6.

FIG. 10 at the time-point of 0 seconds depicts Surgifoam® Powder before adding saline. At the time-point of 2 seconds a drop of saline is likewise added to the powder. The droplet can be recognised as a partly dark zone where the droplet has landed. There is a remarkable difference when comparing with the powder according to the invention, as there still remain unwetted powder within the zone encircled by the droplet. In the Surgifoam® Powder no spreading of the saline-droplet is seen even after 144 seconds, i.e. the diameter of the droplet zone does not increase. Further, it should be noted that the powder at the position of the landing droplet is only partly wetted.

The obtained results from the wetability studies are compiled in the below Table.

| Distance from the centre of the droplet to the edge of the wetted area | | |
|---|---|---|
| Time (seconds) | Powder according to the invention (cm) | Surgifoam ® Powder (cm) |
| 0 | 0 | 0 |
| 2 | 4 | 5.5 |
| 6 | 5 | 5.5 |
| 8 | 7 | 5.5 |
| 10 | 8.75 | 5.5 |
| 20 | 9.5 | 5.5 |
| 30 | 11 | 5.5 |
| 40 | 13 | 5.5 |
| 50 | 13.5 | 5.5 |
| 60 | 14 | 5.5 |

From the above results, as well as from FIGS. 9 and 10, it is evident that the wetability of the powder according to the invention is significantly improved.

Saline Absorption

The amount of absorbed saline was determined by weighing after exposure of the powder to saline for 0.5 minutes, 2 minutes and 5 minutes. The amount of saline absorbed by the powder according to the invention was compared to the amount absorbed by Surgifoam® Powder. The obtained results are compiled in the below Tables.

| Powder according to the invention | | | | |
|---|---|---|---|---|
| | Saline absorbed in gram | | | |
| Powder | 0.5 min | 2 min | 5 min | n = |
| 2 (g) | 3.7 | 7.3 | 9.5 | 5 |
| std. | 0.3 | 0.7 | 0.2 | |

| Surgifoam ® Powder | | | | |
|---|---|---|---|---|
| | Saline absorbed in gram | | | |
| Powder | 0.5 min | 2 min | 5 min | n = |
| 2 (g) | 2.9 | 5.2 | 6.9 | 5 |
| std. | 0.4 | 1.0 | 1.8 | |

The above results show that the powder according to the invention is absorbing saline faster than Surgifoam® Powder and that the absorption capacity is higher. Thus, the absorption properties of the powder according to the invention is significantly improved.

Example 7

In Vitro Coagulation Test in Blood from Humans

The in vitro coagulation properties of the gelatine powder prepared as described in Example 1A above was investigated. The test powder denoted "Test powder I" was sterilised by 25 kGy β-radiation, whereas the test powder denoted "Test powder II" was sterilised by 55 kGy β-radiation Samples of each test powder (30 mg) were placed in tubes and covered with fresh human blood (1 ml) using a ratio of 30 mg test powder/ml blood. The tubes were placed in a water bath at 37° C. and were shaken regularly.

The time needed for total coagulation to occur was recorded for each sample.

Untreated controls, negative controls (treated with pieces of negative control plastic) and positive controls (treated with Fuller's Earth) were also tested.

Each test powder and control was assayed once with blood from four different human beings.

Results

| | Coagulation time (seconds) | | | | | |
|---|---|---|---|---|---|---|
| Treatment | Donor 1 | Donor 2 | Donor 3 | Donor 4 | Mean ± SD | % |
| Untreated control | 355 | 383 | 339 | 374 | 363 ± 20 | 100 |
| Negative control | 366 | 331 | 344 | 220 | 315 ± 65 | 87 |
| Positive control | 101 | 97 | 64 | 74 | 84 ± 18 | 23 |
| Test powder I | 109 | 139 | 99 | 146 | 123 ± 23 | 34 |
| Test powder II | 140 | 202 | 200 | 118 | 165 ± 43 | 45 |

As can be seen from the above coagulation data, the gelatine powder composition exhibits excellent coagulation properties with a coagulation time being in the range of 30-50% of the coagulation time of untreated controls.

Example 8

Evaluation on Haemostatic Efficacy in a Porcine Spleen Model

The objective of this study was to compare the in vivo efficacy of the gelatine powder prepared in Examples 1A and 1B with and without two different adhesive agents (glucose monohydrate and sucrose) when applied to small, freely bleeding incisions made in the spleen of a pig (female pig, 35 kg). The objective was furthermore to obtain knowledge concerning the amount of powder needed per bleeding.

The aim of this animal trial was to compare the efficacy of dry absorbable gelatine powders added no or one of the two different adhesive components. The absorbable gelatine powders were applied dry to freely bleeding incisions made in the spleen of the pig.

Experimental Design

The powder was applied to multiple surgical incisions in the spleen during the testing period. Comparative analysis of the recorded times were conducted and each test was repeated twice. The pigs were anaesthetised and not allowed to recover from anaesthesia.

Sample Preparation

Depending on the extent of bleeding the incision area was treated with either a part or the whole content of a 1 g container of the powder. An amount of the powder adequate to obtain haemostasis was applied with a margin on all sides of about 10 mm.

Surgical Procedure

The primary test parameter was to measure time to haemostasis.

A midline abdominal incision was made to expose the spleen. The size of the incisions was 1.5 cm long and 2 mm deep.

A total of 13 incisions were made in the pig spleen whereof one incision was used as a negative control to demonstrate a consistent bleeding with digital pressure and wetted gauze.

The test powder was applied as fast and deep as possible with a digital pressure for 2 minutes. Haemostasis evaluation was performed every 30 seconds, with an additional 30 seconds of digital pressure, until haemostasis was achieved for 30 seconds. The negative control using saline moistened gauze was performed at the start of the test to demonstrate consistent bleeding of more than 12 minutes in the absence of a haemostatic agent.

Pictures were taken for every 30 seconds documenting the procedure before, during and after to provide examples of handling characteristics of the tested haemostatics. Pictures of the negative control are taken until 12 minutes.

Results

Figure 7:
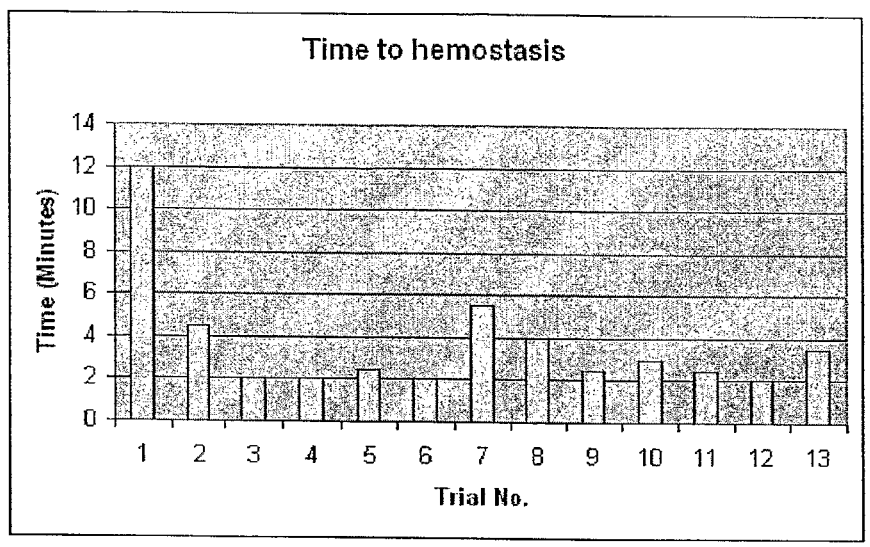

The obtained results are presented in the below table. In addition, the obtained data are shown graphically in FIG. 7.

| Trial no. | Test powder | Haemostasis Time |
|---|---|---|
| 1 | Negative control (standard gauze and sterile saline) | >12 min. |
| 2 | Gelatine powder from Example 2A | 4.5 min.[1] |
| 3 | Gelatine powder from Example 2A | 2 min. |
| 4 | Gelatine powder from Example 2B | 2 min. |
| 5 | Gelatine powder from Example 2B | 2.5 min. |
| 6 | Gelatine powder from Example 2A (glucose added) | 2 min.[1] |
| 7 | Gelatine powder from Example 2A (glucose added) | 5.5 min.[2] |
| 8 | Gelatine powder from Example 2B (glucose added) | 4 min. |
| 9 | Gelatine powder from Example 2B (glucose added) | 2.5 min. |
| 10 | Gelatine powder from Example 2A (sucrose added) | 3 min. |
| 11 | Gelatine powder from Example 2A (sucrose added) | 2.5 min. |
| 12 | Gelatine powder from Example 2B (sucrose added) | 2 min. |
| 13 | Gelatine powder from Example 2B (sucrose added) | 3.5 min.[3] |

[1] Only bleeding in the corner without powder
[2] Test article applied on bleeding spot without powder
[3] Powder applied on a very inclined surface and the powder ran off The gelatine powder composition achieved haemostasis in an average time of 3.0 minutes compared to the negative control; which failed to achieve haemostasis within 12 minutes. There was however no difference between the test articles with or without the two different adhesive components.

The invention claimed is:

1. A powder delivery system comprising a chamber storing a haemostatic composition comprising dry gelatin powder having a mean particle size in the range of 30-250 μm and hyaluronic acid, said chamber having at least one discharge opening sized for distributing said composition.

2. The delivery system according to claim 1, wherein said discharge opening is sized for distributing said composition to a surface in controlled amounts.

3. The delivery system according to claim 1 or 2, further comprising an elongated tip for distributing the composition.

4. The delivery system according to claim 1, wherein the delivery system is manually operable.

5. The delivery system according to claim 4, wherein the delivery system is manually operable by shaking or squeezing the system.

6. The delivery system according to claim 1, wherein the delivery system comprises a resilient chamber or bellows.

7. The delivery system according to claim 6, wherein the resilient chamber or bellows is adapted to be manually activated to discharge at least part of the composition.

8. The delivery system according to claim 1, further comprising a protective structure arranged at the discharge opening.

9. The delivery system according to claim 8, wherein the protective structure is a skirt portion arranged to extend from the discharge opening.

10. The delivery system according to claim 1, wherein the powder has a particle size distribution where at least 80% by volume of the particles have a particle size of 30 to 170 μm.

11. The delivery system according to claim 1, wherein the moisture content of the powder is at the most 20% (w/w).

12. The delivery system according to claim 1, wherein said powder has a poured density in the range of 0.05 to 0.3 g/ml.

13. The delivery system according to claim 1, wherein said composition further comprises an agent which improves the adhesive properties of said composition.

14. The delivery system according to claim 13, wherein said agent is selected from the group consisting of sucrose, glucose, and combinations thereof.

15. The delivery system according to claim 13 or 14, wherein said agent is admixed with said powder.

16. The delivery system according to claim 13 or 14, wherein said agent is coated on the surface of said powder.

17. The delivery system according to claim 13, wherein said composition comprises 0.1 to 50% (w/w) of said agent, calculated on the total weight of the composition.

18. The delivery system according to claim 1, wherein said composition further comprises a coagulation factor.

19. The delivery system according to claim 18, wherein said coagulation factor is thrombin.

20. The delivery system according to claim 1, wherein said composition does not contain a coagulation factor.

21. The delivery system according to claim 1, wherein said delivery system does not contain any propellants.

22. A method for promoting haemostasis in a patient in need thereof, said method comprising spraying a haemostatic powder composition comprising gelatin having a mean particle size in the range of 30-250 μm and hyaluronic acid, wherein said powder is dry, onto at least a portion of an area where bleeding occurs.

23. The delivery system according to claim 1, wherein the moisture content of the powder is at the most 15% (w/w).

24. The delivery system according to claim 13, wherein said agent is selected from the group consisting of chondroitin, chondroitin sulfate, dermatan sulfate and keratan sulfate; aminated dextrans including DEAE-dextran; aminated starch, aminated glycogen, aminated cellulose, aminated pectin, and salts, complexes, and mixtures thereof.

25. The delivery system according to claim 7, wherein the manual activation occurs by finger pressure.

* * * * *